United States Patent
Gaudino et al.

(10) Patent No.: US 7,560,462 B2
(45) Date of Patent: Jul. 14, 2009

(54) COMPOUNDS USEFUL FOR INHIBITING CHK1

(75) Inventors: John Joseph Gaudino, Longmont, CO (US); Adam Wade Cook, Broomfield, CO (US)

(73) Assignee: ICOS Corporation, Bothell, WA (US)

( * ) Notice: Subject to any disclaimer, the term of this patent is extended or adjusted under 35 U.S.C. 154(b) by 0 days.

(21) Appl. No.: 11/630,626

(22) PCT Filed: Jul. 1, 2005

(86) PCT No.: PCT/US2005/023554

§ 371 (c)(1),
(2), (4) Date: Oct. 24, 2007

(87) PCT Pub. No.: WO2006/014359

PCT Pub. Date: Feb. 9, 2006

(65) Prior Publication Data

US 2008/0214573 A1    Sep. 4, 2008

Related U.S. Application Data

(60) Provisional application No. 60/585,292, filed on Jul. 2, 2004.

(51) Int. Cl.
| | |
|---|---|
| A61K 31/497 | (2006.01) |
| C07D 401/10 | (2006.01) |
| C07D 403/10 | (2006.01) |
| C07D 405/10 | (2006.01) |
| C07D 409/10 | (2006.01) |
| C07D 411/10 | (2006.01) |
| C07D 413/10 | (2006.01) |
| C07D 417/10 | (2006.01) |
| C07D 419/10 | (2006.01) |
| A61P 35/00 | (2006.01) |
| C07D 241/14 | (2006.01) |
| C07D 241/16 | (2006.01) |
| C07D 241/20 | (2006.01) |
| C07D 211/70 | (2006.01) |
| C07D 211/84 | (2006.01) |
| C07D 213/89 | (2006.01) |

(52) U.S. Cl. ............. 514/255.05; 544/405; 544/406; 544/407; 544/408; 544/336; 546/329; 548/235; 548/202; 548/201; 548/205; 548/200; 564/74; 568/940; 556/422

(58) Field of Classification Search ............ 514/255.04, 514/255.05; 544/405
See application file for complete search history.

(56) References Cited

FOREIGN PATENT DOCUMENTS

| WO | WO 02/070494 | 9/2002 |
|---|---|---|
| WO | WO 03/051366 | 6/2003 |
| WO | WO 2004/014876 | 2/2004 |

OTHER PUBLICATIONS

Kim, et al., Eur. J. Surg. Oncol., vol. 33, # 5, Jun. 2007, 580-585.*
Jin, et al., Genes & Devel. 17:3062-3074, 2003.*
Verlinden, et al., Cancer Res. 67, 6574-6581, Jul. 15, 2007.*
Tabernero, et al., Ann. Oncol. 2005 16(11):1740-1748.*
Sturgeon, et al., Cell Cycle, 2007, vol. 6 # 5, 572-575.*
Kurihara, Takashi, et al., "Organic nonlinear optical material with high third harmonic generation", Chemical Abstract Service, XP002363142, 1987.
Lu, Xiaoling, et al., "Thermolysis of Benzannulated Enyne-Carbodiimides. Application in the Synthesis of Pyrido '1',2':1.2!pyrimido'4,5-b!indoles and Related Heteroaromatic Compounds" Journal of Organic Chemistry, 67(22), 2002, p. 7797-7801.

* cited by examiner

Primary Examiner—Mark L Berch
Assistant Examiner—Cecilia M Jaisle
(74) Attorney, Agent, or Firm—Elizabeth A. McGraw; Danica Hostettler

(57) ABSTRACT

Substituted urea compounds useful in the treatment of diseases and $C_{1-3}$alkyleneOR$^3$ conditions related to DNA damage or lesions in DNA replication are disclosed formula (I), wherein $X^1$ is null, —O—, —S—, —CH$_2$—, or —N(R$^1$)—; $X^2$ is —O—, . -£>. -, or —N(R$^1$)—,— . . Y xs 0 or S; or =y represents two hydrogen atoms attached to a common carbon atom, —W is selected from the group consisting of heteroaryl, aryl, heterocycloalkyl, cycloalkyl, and $_{C1-6}$alkyl substituted with a heteroaryl. or aryl group; R$^6$ is —C≡C—R$^7$ or heteroaryl; R$^8$, R$^9$, and R$^{10}$, independently, are selected from the group consisting of halo, optionally substituted $C_{1-6}$alkyl, $C_{2-6}$alkenyl, $C_{2-6}$alkynyl, OCP$_3$, CF$_3$, NO$_2$, CN, NC, N(R$^3$)$_2$, OR$^3$, CO$_2$R$^3$, C(O)N (R$^3$)$_2$, C(O)R$^3$, N(R$^1$)COR$^3$, N(R$^1$)C(O)OR$^3$, N(R$^8$)C(O)OR$^3$, N(R$^1$)C(O)C$_{1-3}$alkyleneC(O)R$^3$, N(R$^1$)C(O)C$_{1-3}$alkyleneC(O)OR$^3$, N(R$^1$)C(O)C$_{1-3}$alkyleneOR$^3$, N(R$^1$)C(O)C$_{1-3}$alkyleneNHC(O)OR$^3$, N(R$^1$)C(O)C$_{1-3}$alkyleneSO$_2$.NR$^3$, $C_{1-3}$alkyleneOR$^3$, and SR$^3$; Methods of making the compounds, and their use as therapeutic agents, for example, in treating cancer and other diseases characterized by defects in DNA replication, chromosome segregation, or cell division also are disclosed.

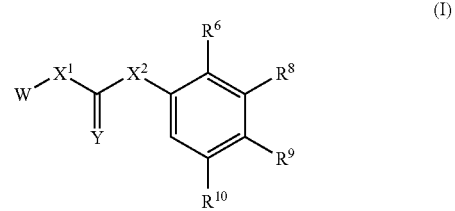

(I)

3 Claims, No Drawings

COMPOUNDS USEFUL FOR INHIBITING CHK1

CROSS-REFERENCE TO RELATED APPLICATION

This U.S. national phase application of International Application No. PCT/US2005/023554, filed Jul. 1, 2005, which claims benefit of U.S. provisional patent application No. 60/585,292, filed Jul. 2, 2004.

FIELD OF THE INVENTION

The present invention relates to compounds useful for inhibiting enzymes that maintain and repair the integrity of genetic material. More particularly, the present invention relates to a series of aryl- and heteroaryl-substituted urea compounds, methods of making the compounds, and their use as therapeutic agents, for example, in treating cancer and other diseases characterized by defects in deoxyribonucleic acid (DNA) replication, chromosome segregation, or cell division.

BACKGROUND OF THE INVENTION

A large variety of diseases, conditions, and disorders (hereinafter "indications") are characterized as involving aberrantly proliferating cells. As used herein, "aberrantly proliferating cells" (or "aberrant cell proliferation") means cell proliferation that deviates from the normal, proper, or expected course. For example, aberrant cell proliferation includes inappropriate proliferation of cells wherein DNA or other cellular components have become damaged or defective. Aberrant cell proliferation also includes indications caused by, mediated by, or resulting in inappropriately high levels of cell division, inappropriately low levels of cell death (e.g., apoptosis), or both. Such indications can be characterized, for example, by single or multiple local abnormal proliferations of cells, groups of cells or tissue(s), and include cancerous (benign or malignant) and noncancerous indications.

By definition, all cancers (benign and malignant) involve some form of aberrant cell proliferation. Some noncancerous indications also involve aberrant cell proliferation. Examples of noncancerous indications involving aberrant cell proliferation include rheumatoid arthritis, psoriasis, vitiligo, Wegener's granulomatosis, and systemic lupus.

One approach to treating indications involving aberrantly proliferating cells involves the use of DNA damaging agents. These agents are designed to kill aberrantly proliferating cells by disrupting vital cellular processes such as DNA metabolism, DNA synthesis, DNA transcription, and microtubule-spindle formation. They also can operate, for example, by introducing lesions into DNA that perturb chromosomal structural integrity. DNA damaging agents are designed and administered in ways that attempt to induce maximum damage and consequent cell death in aberrantly proliferating cells with a minimum damage to normal, healthy cells.

A large variety of DNA damaging agents have been developed to date, including chemotherapeutics and radiation, and others are in development. Unfortunately, the effectiveness of DNA damaging agents in treating conditions involving aberrant cell proliferation have been less than desired, particularly in the treatment of cancer. The selectivity of such agents for aberrantly proliferating cells over healthy cells (sometimes referred to as the therapeutic index) often is marginal.

Moreover, all cells have sensing and repair mechanisms that can work at cross purposes to DNA damaging agents. Such sensing mechanisms, called cell cycle checkpoints, help to maintain the order of the various cell replication stages and to ensure that each step is executed with high fidelity (Hartwell et al., *Science*, 246:629-34 (1989); Weinert et al., *Genes Dev.*, 8:652 (1994)). When cells detect DNA damage, including damage purposefully induced by DNA damaging agents, certain signaling pathways activate cell cycle checkpoints and the cell replication cycle temporarily ceases ("arrests"). This arrest allows cells time to repair their DNA, often to a degree sufficient to allow the affected cells to continue to survive and proliferate. In the case of aberrantly proliferating cells, this repair is unwanted, as it may undermine efforts to induce DNA damage sufficient to kill such cells.

For example, the chemotherapeutic agent called GEMZAR™ (gemcitabine, or 2',2' difluoro-2'-deoxycytidine) damages DNA by incorporating itself into DNA during synthesis. Left unrepaired, damaged DNA generally is rendered incapable of sustaining life. In many targeted cells, however, cell cycle checkpoints detect the improperly made (or otherwise damaged) DNA. The activated cell cycle checkpoints trigger cell cycle arrest for a time sufficient to allow damaged DNA to be repaired. This is one way in which aberrantly proliferating cells are theorized to resist the cell-killing effect of DNA-damaging agents such as chemotherapeutics, radiation, and other therapies.

Other DNA-damaging agents cause tumor cells to arrest in S-phase. Tumor cells have been observed to resist certain chemotherapeutics simply by arresting in S phase while the chemotherapeutic agent is being administered. Then, as soon as the drug is removed, DNA damage is repaired, cell cycle arrest ceases, and the cells progress through the remainder of the cell cycle (Shi et al., *Cancer Res.* 61:1065-72, 2001). Other therapeutics cause cell cycle-arrest at other checkpoints, including G1 and G2. Inhibition of various DNA damage checkpoints therefore is expected to assist in preventing cells from repairing therapeutically induced DNA damage and to sensitize targeted cells to DNA damaging agents. Such sensitization is in turn expected to increase the therapeutic index of these therapies.

The cell cycle is structurally and functionally the same in its basic process and mode of regulation across all eukaryotic species. The mitotic (somatic) cell cycle consists of four phases: the G1 (gap) phase, the S (synthesis) phase, the G2 (gap) phase, and the M (mitosis) phase. The G1, S, and G2 phases are collectively referred to as interphase of the cell cycle. During the G1 phase, biosynthetic activities of the cell progress at a high rate. The S phase begins when DNA synthesis starts, and ends when the DNA content of the nucleus of the cell has been replicated and two identical sets of chromosomes are formed.

The cell then enters the G2 phase, which continues until mitosis starts. In mitosis, the chromosomes pair and separate, two new nuclei form, and cytokinesis occurs in which the cell splits into two daughter cells each receiving one nucleus containing one of the two sets of chromosomes. Cytokinesis terminates the M phase and marks the beginning of interphase of the next cell cycle. The sequence in which cell cycle events proceed is tightly regulated, such that the initiation of one cell cycle event is dependent on the completion of the prior cell cycle event. This allows fidelity in the duplication and segregation of genetic material from one generation of somatic cells to the next.

It has been reported that cell cycle checkpoints comprise at least three distinct classes of polypeptides, which act sequentially in response to cell cycle signals or defects in chromosomal mechanisms (Carr, *Science,* 271:314-15, 1996). The first class is a family of proteins that detect or sense DNA damage or abnormalities in the cell cycle. These sensors include Ataxia-telangiectasia Mutated protein (Atm) and Ataxia-Telangiectasia Rad-related protein (Atr). The second class of polypeptides amplify and transmit the signal detected by the detector and is exemplified by Rad53 (Alen et al., *Genes Dev.* 8:2416-88, 1994) and Chk1. A third class of polypeptides includes cell cycle effectors, such as p53, which mediate a cellular response, for example, arrest of mitosis and apoptosis.

Much of the current understanding of the function of cell cycle checkpoints has been derived from the study of tumor derived cell lines. In many cases, tumor cells have lost key cell cycle check points (Hartwell et al., *Science* 266:1821-28, 1994). It has been reported that a key step in the evolution of cells to a neoplastic state is the acquisition of mutations that inactivate cell cycle checkpoint pathways, such as those involving p53 (Weinberg, *Cell* 81:323-30, 1995; Levine, *Cell* 88:3234-31, 1997). Loss of these cell cycle checkpoints results in the replication of tumor cells despite DNA damage.

Noncancerous tissue, which has intact cell cycle checkpoints, typically is insulated from temporary disruption of a single checkpoint pathway. Tumor cells, however, have defects in pathways controlling cell cycle progression such that the perturbation of additional checkpoints renders them particularly sensitive to DNA damaging agents. For example, tumor cells that contain mutant p53 are defective both in the G1 DNA damage checkpoint and in the ability to maintain the G2 DNA damage checkpoint (Bunz et al., *Science,* 282:1497-501, 1998). Checkpoint inhibitors that target initiation of the G2 checkpoint or the S phase checkpoint are expected to further cripple the ability of these tumor cells to repair DNA damage and, therefore, are candidates to enhance the therapeutic index of both radiation and systemic chemotherapy (Gesner, Abstract at SRI Conference: Protein Phosphorylation and Drug Discovery World Summit, March 2003).

In the presence of DNA damage or any impediment to DNA replication, the checkpoint proteins Atm and Atr initiate a signal transduction pathway leading to cell cycle arrest Atm has been shown to play a role in a DNA damage checkpoint in response to ionizing radiation. Atr is stimulated by agents that cause double strand DNA breaks, single strand DNA breaks, and agents that block DNA radiation.

Chk1 is a protein kinase that lies downstream from Atm and/or Atr in the DNA damage checkpoint signal transduction pathway (Sanchez et al., *Science,* 277:1497-501, 1997; U.S. Pat. No. 6,218,109). In mammalian cells, Chk1 is phosphorylated in response to agents that cause DNA damage including ionizing radiation, ultraviolet (UV) light, and hydroxyurea (Sanchez et al., supra; Lui et al., *Genes Dev.,* 14:1448-59, 2000). This phosphorylation, which activates Chk1 in mammalian cells, is dependent on Atm (Chen et al., *Oncogene,* 18:249-56, 1999) and Atr (Lui et al., supra). Furthermore, Chk1 has been shown to phosphorylate both weel (O'Connell et al., *EMBO J.,* 16:545-54, 1997) and Pds1 (Sanchez et al., *Science,* 286:1166-71, 1999), gene products known to be important in cell cycle control.

These studies demonstrate that mammalian Chk1 plays a role in the Atm dependent DNA damage checkpoint leading to arrest at S phase. A role for Chk1 in the S phase mammalian cells has recently been elucidated (Feijoo et al., *J. Cell. Biol.,* 154:913-23, 2001; Zhao et al., *Proc. Nat. Acad. Sci. USA,* 99:14795-800, 2002; Xiao et al., *J Biol. Chem.,* 278(24): 21767-773, 2003; Sorensen et al., *Cancer Cell,* 3(3):247-58, 2003) highlighting the role of Chk1 in monitoring the integrity of DNA synthesis. Chk1 invokes an S-phase arrest by phosphorylating Cdc25A, which regulates cyclinA/cdk2 activity (Xiao et al., supra and Sorensen et al., supra). Chk1 also invokes a G2 arrest by phosphorylating and inactivating Cdc25C, the dual specificity phosphatase that normally dephosphorylates cyclin-B/cdc2 (also known as Cdk1) as cells progress from G2 into mitosis (Fernery et al., *Science,* 277:1495-7, 1997; Sanchez et al., supra; Matsuoka et al., *Science,* 282:1893-97, 1998; and Blasina et al., *Curr. Biol.,* 9:1-10, 1999). In both cases, regulation of Cdk activity induces a cell cycle arrest to prevent cells from entering mitosis in the presence of DNA damage or unreplicated DNA.

Additional classes of cell cycle checkpoint inhibitors operate at either the G1 or G2/M phase. UCN-01, or 7-hydroxystaurosporine, originally was isolated as a nonspecific kinase inhibitor having its primary effect on protein kinase C, but recently it has been found to inhibit the activity of Chk1 and abrogate the G2 cell cycle checkpoint (Shi et al., supra). Thus, because UCN-01 is a nonselective Chk1 inhibitor, it is toxic to cells at high doses. At low doses, it nonspecifically inhibits many cellular kinases and also inhibits the G1 checkpoint (Tenzer et al., *Curr. Med. Chem. Anti-Cancer Agents,* 3:35-46, 2003).

UCN-01 has been used in conjunction with cancer therapies, such as radiation, the anti-cancer agent camptothecin (Tenzer et al., supra), and gemcitabine (Shi et al., supra), with limited success. In addition, UCN-01 has been used to potentiate the effects of temozolomide (TMZ)-induced DNA mismatch repair (MMR) in glioblastoma cells (Hirose et al., *Cancer Res.,* 61:5843-49, 2001). In the clinic, UCN-01 is not an effective chemotherapeutic as expected, possibly due to a failure in treatment scheduling and a lack of identification of particular key molecular targets (Grant et al., *Drug Resistance Updates,* 6:15-26, 2003). Thus, Mack et al. report cell cycle-dependent potentiation of cisplatin by UCN-01 in a cultured nonsmall-cell lung carcinoma cell line, but do not identify with specificity the key cell cycle checkpoint(s) targeted by UCN-01. (Mack et al., *Cancer Chemother. Pharmacol.,* 51(4):337-48, 2003).

Several other strategies exist for sensitizing tumor cells to treatment with cell cycle affecting chemotherapeutics. For example, administration of 2-aminopurine abrogates multiple cell cycle-checkpoint mechanisms, such as mimosine-induced G1 arrest or hydroxyurea-induced S phase arrest, allowing the cell to progress into and through mitosis (Andreassen et al., *Proc Natl Acad Sci USA,* 86:2272-76, 1992). Caffeine, a methylxanthine, has also been used to enhance cytotoxicity of DNA-damaging agents, such as cisplatin and ionizing radiation, by mediating progression through the G2 checkpoint and thereby inducing cell death. (Bracey et al., *Clin. Cancer Res.,* 3:1371-81, 1997). However, the dose of caffeine used to accomplish the cell cycle abrogation exceeds clinically acceptable levels and is not a viable therapeutic option. Additionally, antisense nucleotides to Chk1 kinase have been used to increase sensitivity to the topoisomerase inhibitor BNP1350 (Yin et al., *Biochem. Biophys. Res. Commun.,* 295:435-44, 2002), but demonstrate problems typically associated with antisense treatment and gene therapy.

Chk1 inhibitors have been disclosed, including aryl- and heteroaryl-substituted urea compounds described in U.S. patent application Ser. No. 10/087,715 and U.S. Provisional Patent Application Nos. 60/583,080 and 60/602,968; diaryl urea compounds described in U.S. Patent Publication No. 2004/0014765, U.S. Patent Publication No. 2003/199511, U.S. Patent Publication No. 2004/0014765, and WO 03/101444; methylxanthines and related compounds described in Fan et al., *Cancer Res.* 55:1649-54, 1995; ureidothiphenes described in WO 03/029241 and WO 03/028731; N-pyrrolopyridinyl carboxamides described in WO 03/028724; antisense Chk1 oligonucleotides described in WO 01/57206 and U.S. Pat. No. 6,211,164; Chk1 receptor antagonists described in WO 00/16781; heteroaromatic carboxamide derivatives described in WO 03/037886; aminothiophenes described in WO 03/029242; (indazolyl)benzimidazoles described in WO 03/004488; benzimidazole quinolinones described in U.S. Patent Publication No. 2004/0092535 and WO 04/018419; heterocyclic-hydroxyiminofluorenes described in WO 02/16326; scytoneman derivatives, such as scytonemin, described in U.S. Pat. No. 6,495,586; heteroarylbenzamides described in WO 01/53274; indazoles described in WO 01/53268; indolacarbazoles described in Tenzer et al., supra; chromane derivatives described in WO 02/070515; paullones described in Schultz et al., *J. Med. Chem.*, Vol: 2909-19, 1999; indenopyrazoles described in WO 99/17769; flavones described in Sedlacek et al., *Int J. Oncol.*, 9:1143-68, 1996; peptide derivatives of peptide loop of serine threonine kinases described in WO 98/53050; oxindoles described in WO 03/051838; diazepinoindolones described in WO 04/063198; pyrimidines described in WO 04/048343; urea compounds described in WO 04/014876; and pyrrolocarbazoles, benzofuroisoindoles, and azacyclopentafluorenes described in WO 03/091255.

However, a need still exists in the art for effective and selective inhibitors of Chk1. The present invention addresses this and other needs.

SUMMARY OF THE INVENTION

The present invention relates to inhibitors of the checkpoint kinase Chk1. The present Chk1 inhibitors are useful in treating indications involving aberrant cell proliferation, and as chemosensitizing and radiosensitizing agents in the treatment of indications related to DNA damage or lesions in DNA replication.

Therefore, one aspect of the present invention is to provide compounds of structural formula (I). The compounds are useful in a method of inhibiting Chk1 comprising a step of administering an effective amount of a compound of structural formula (I) to an individual in need thereof.

Compounds of formula (I) have a structural formula:

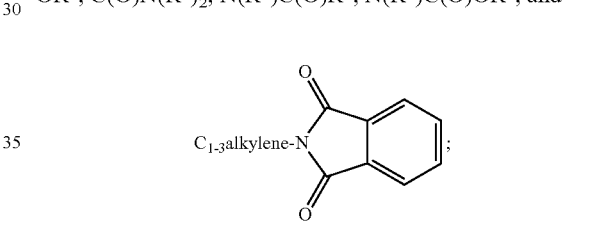

wherein $X^1$ is null, —O—, —S—, —CH$_2$—, or —N(R$^1$)—;

$X^2$ is —O—, —S—, or —N(R$^1$)—;

Y is O or S; or =Y represents two hydrogen atoms attached to a common carbon atom;

W is selected from the group consisting of heteroaryl, aryl, heterocycloalkyl, cycloalkyl, and $C_{1-6}$alkyl substituted with a heteroaryl or aryl group, wherein said aryl group W is optionally substituted with one to four substituents represented by $R^2$, said heteroaryl group W is optionally substituted with one to four substituents represented by $R^5$, and said heterocycloalkyl and cycloalkyl groups W are optionally substituted with one or two $C_{1-6}$alkyl substituents;

$R^1$ is selected from the group consisting of hydro, $C_{1-6}$alkyl, $C_{2-6}$alkenyl, $C_{2-6}$alkynyl, and aryl;

$R^2$ is selected from the group consisting of halo, optionally substituted $C_{1-6}$alkyl, $C_{2-6}$alkenyl, OCF$_3$, NO$_2$, CN, NC, N(R$^3$)$_2$, OR$^3$, CO$_2$R$^3$, C(O)N(R$^3$)$_2$, C(O)R$^3$, N(R$^1$)COR$^3$, N(R$^1$)C(O)OR$^3$, N(R$^1$)C(O)C$_{1-6}$alkyleneC(O)R$^3$, N(R$^1$)C(O)C$_{1-6}$alkyleneC(O)OR$^3$, N(R$^1$)C(O)C$_{1-6}$alkyleneOR$^3$, N(R$^1$)C(O)C$_{1-6}$alkyleneNHC(O)OR$^3$, N(R$^1$)C(O)C$_{1-6}$alkyleneSO$_2$NR$^3$, C$_{1-6}$alkyleneOR$^3$, and SR$^3$;

$R^3$ is selected from the group consisting of hydro, halo, $C_{1-6}$alkyl, $C_{2-6}$alkenyl, cycloalkyl, aryl, heteroaryl, SO$_2$R$^4$, $C_{1-6}$alkyl substituted with one or more of halo, hydroxy, aryl, heteroaryl, heterocycloalkyl, N(R$^4$)$_2$, and SO$_2$R$^4$, $C_{1-6}$alkylenearyl, $C_{1-6}$alkyleneheteroaryl, $C_{1-6}$alkyleneC$_{3-8}$heterocycloalkyl, $C_{1-6}$alkyleneSO$_2$aryl, optionally substituted $C_{1-6}$alkyleneN(R$^4$)$_2$, OCF$_3$, $C_{1-6}$alkyleneN(R$^4$)$_3^+$, C$_{3-8}$heterocycloalkyl, and CH(C$_{1-6}$alkyleneN(R$^4$)$_2$)$_2$, or two $R^3$ groups are taken together to form an optionally substituted 3- to 8-membered aliphatic ring;

$R^4$ is selected from the group consisting of hydro, $C_{1-6}$alkyl, cycloalkyl, aryl, heteroaryl, $C_{1-6}$alkylenearyl, and SO$_2$C$_{1-6}$alkyl, or two $R^4$ groups are taken together to form an optionally substituted 3- to 8-membered ring;

$R^5$ is selected from the group consisting of $C_{1-6}$alkyl, $C_{2-6}$alkynyl, aryl, heterocycloalkyl, N(R$^3$)$_2$, OR$^3$, halo, N$_3$, CN, $C_{1-6}$alkylenearyl, $C_{1-6}$alkyleneN(R$^3$)$_2$, C(O)R$^3$, C(O)OR$^3$, C(O)N(R$^3$)$_2$, N(R$^1$)C(O)R$^3$, N(R$^1$)C(O)OR$^3$, and

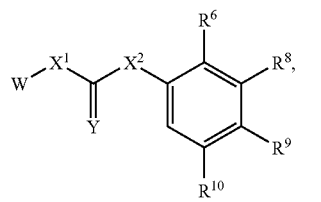

$R^6$ is —C≡C—R$^7$ or heteroaryl;

$R^7$ is selected from the group consisting of hydro, $C_{1-6}$alkyl, aryl, $C_{1-6}$alkylenearyl, heteroaryl, $C_{1-6}$alkyleneheteroaryl, alkoxy;

$R^8$, $R^9$, and $R^{10}$, independently, are selected from the group consisting of halo, optionally substituted $C_{1-6}$alkyl, $C_{2-6}$alkenyl, $C_{2-6}$alkynyl, OCF$_3$, CF$_3$, NO$_2$, CN, NC, N(R$^3$)$_2$, OR$^3$, CO$_2$R$^3$, C(O)N(R$^3$)$_2$, C(O)R$^3$, N(R$^1$)COR$^3$, N(R$^1$)C(O)—OR$^3$, N(R$^8$)C(O)OR$^3$, N(R$^1$)C(O)C$_{1-3}$alkyleneC(O)R$^3$, N(R$^1$)C(O)—C$_{1-3}$alkyleneC(O)OR$^3$, N(R$^1$)C(O)C$_{1-3}$alkyleneOR$^3$, N(R$^1$)C(O)—C$_{1-3}$alkyleneNHC(O)OR$^3$, N(R$^1$)C(O)C$_{1-3}$alkyleneSO$_2$NR$^3$, C$_{1-3}$alkyleneOR$^3$, and SR$^3$;

or a pharmaceutically acceptable salt, or prodrug, or solvate thereof.

Another aspect of the present invention is to provide pharmaceutical compositions comprising one or more compound of structural formula (I), and use of the compositions in a therapeutic treatment of an indication, wherein inhibition of Chk1, in vivo or ex vivo, provides a therapeutic benefit or is of research or diagnostic interest.

Yet another aspect of the present invention is to provide a method of sensitizing cells in a subject undergoing a chemotherapeutic or radiotherapeutic treatment for an indication comprising administration of a compound of structural formula (I) in combination with a chemotherapeutic agent, a radiotherapeutic agent, or both, to the individual. A nonlimiting indication treated by this method is a cancer.

Another aspect of the present invention is to provide a method of inhibiting or preventing aberrant cell proliferation. In one embodiment, a method comprises contacting a cell population comprising aberrantly proliferating cells with at least one Chk1 activator in an amount and for a time sufficient to substantially synchronize cell cycle arrest among the aberrantly proliferating cells. Upon achieving substantial synchronization of cell cycle arrest in the cell population, the cell population is contacted with at least one Chk1 inhibitor in an amount and for a time sufficient to substantially abrogate the cell cycle arrest.

Another aspect of the present invention is to provide an article of manufacture for human pharmaceutical use comprising:

(a) a pharmaceutical composition comprising a compound of structural formula (I);

(b) a package insert informing that the composition is useful in the treatment of indications involving aberrant cell proliferation; and, optionally, (c) a container.

Another aspect of the present invention is to provide:

(a) pharmaceutical composition comprising a compound of structural formula (I);

(b) a package insert informing that the composition is useful as a chemosensitizer or radiosensitizer in a treatment of an indication related to DNA lesions or DNA replication; and, optionally, (c) a container.

These and other aspects of the present invention will become apparent from the following detailed description.

DETAILED DESCRIPTION OF THE PREFERRED EMBODIMENTS

Compounds of the present invention have a structural formula (I):

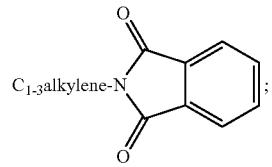

(I)

wherein $X^1$ is null, —O—, —S—, —CH$_2$—, or —N(R$^1$)—;

$X^2$ is —O—, —S—, or —N(R$^1$)—;

Y is O or S; or =Y represents two hydrogen atoms attached to a common carbon atom;

W is selected from the group consisting of heteroaryl, aryl, heterocycloalkyl, cycloalkyl, and $C_{1-6}$alkyl substituted with a heteroaryl or aryl group, wherein said aryl group W is optionally substituted with one to four substituents represented by $R^2$, said heteroaryl group W is optionally substituted with one to four substituents represented by $R^5$, and said heterocycloalkyl and cycloalkyl groups W are optionally substituted with one or two $C_{1-6}$alkyl substituents;

$R^1$ is selected from the group consisting of hydro, $C_{1-6}$alkyl, $C_{2-6}$alkenyl, $C_{2-6}$alkynyl, and aryl;

$R^2$ is selected from the group consisting of halo, optionally substituted $C_{1-6}$alkyl, $C_{2-6}$alkenyl, OCF$_3$, NO$_2$, CN, NC, N(R$^3$)$_2$, OR$^3$, CO$_2$R$^3$, C(O)N(R$^3$)$_2$, C(O)R$^3$, N(R$^1$)COR$^3$, N(R$^1$)C(O)OR$^3$, N(R$^1$)C(O)C$_{1-6}$alkyleneC(O)R$^3$, N(R$^1$)C(O)C$_{1-6}$alkyleneC(O)OR$^3$, N(R$^1$)C(O)C$_{1-6}$alkyleneOR$^3$, N(R$^1$)C(O)C$_{1-6}$alkyleneNHC(O)OR$^3$, N(R$^1$)C(O)C$_{1-6}$alkyleneSO$_2$NR$^3$, $C_{1-6}$alkyleneOR$^3$, and SR$^3$;

$R^3$ is selected from the group consisting of hydro, halo, $C_{1-6}$alkyl, $C_{2-6}$alkenyl, cycloalkyl, aryl, heteroaryl, SO$_2$R$^4$, $C_{1-6}$alkyl substituted with one or more of halo, hydroxy, aryl, heteroaryl, heterocycloalkyl, N(R$^4$)$_2$, and SO$_2$R$^4$, $C_{1-6}$alkylenearyl, $C_{1-6}$alkyleneheteroaryl, $C_{1-6}$alkyleneC$_{3-8}$heterocycloalkyl, $C_{1-6}$alkyleneSO$_2$aryl, optionally substituted $C_{1-6}$alkyleneN(R$^4$)$_2$, OCF$_3$, $C_{1-6}$alkyleneN(R$^4$)$_3^+$, $C_{3-8}$heterocycloalkyl, and CH($C_{1-6}$alkyleneN(R$^4$)$_2$)$_2$, or two R$^3$ groups are taken together to form an optionally substituted 3- to 8-membered aliphatic ring;

$R^4$ is selected from the group consisting of hydro, $C_{1-6}$alkyl, cycloalkyl, aryl, heteroaryl, $C_{1-6}$alkylenearyl, and SO$_2$C$_{1-6}$alkyl, or two R$^4$ groups are taken together to form an optionally substituted 3- to 8-membered ring;

$R^5$ is selected from the group consisting of $C_{1-6}$alkyl, $C_{2-6}$alkynyl, aryl, heterocycloalkyl, N(R$^3$)$_2$, OR$^3$, halo, N$_3$, CN, $C_{1-6}$alkylenearyl, $C_{1-6}$alkyleneN(R$^3$)$_2$, C(O)R$^3$, C(O)OR$^3$, C(O)N(R$^3$)$_2$, N(R$^1$)C(O)R$^3$, N(R$^1$)C(O)OR$^3$, and

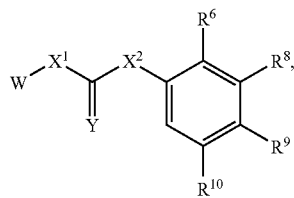

$R^6$ is —C≡C—R$^7$ or heteroaryl;

$R^7$ is selected from the group consisting of hydro, $C_{1-6}$alkyl, aryl, $C_{1-6}$alkylenearyl, heteroaryl, $C_{1-6}$alkyleneheteroaryl, alkoxy;

$R^8$, $R^9$, and $R^{10}$, independently, are selected from the group consisting of halo, optionally substituted $C_{1-6}$alkyl, $C_{2-6}$alkenyl, $C_{2-6}$alkynyl, OCF$_3$, CF$_3$, NO$_2$, CN, NC, N(R$^3$)$_2$, OR$^3$, CO$_2$R$^3$, C(O)N(R$^3$)$_2$, C(O)R$^3$, N(R$^1$)COR$^3$, N(R$^1$)C(O)—OR$^3$, N(R$^8$)C(O)OR$^3$, N(R$^1$)C(O)C$_{1-3}$alkyleneC(O)R$^3$, N(R$^1$)C(O)—C$_{1-3}$alkyleneC(O)OR$^3$, N(R$^1$)C(O)C$_{1-3}$alkyleneOR$^3$, N(R$^1$)C(O)—C$_{1-3}$alkyleneNHC(O)OR$^3$, N(R$^1$)C(O)C$_{1-3}$alkyleneSO$_2$NR$^3$, $C_{1-3}$alkyleneOR$^3$, and SR$^3$;

and a pharmaceutically acceptable salt, or prodrug, or solvate thereof.

Preferred compounds of the present invention are those wherein $X^1$ and $X^2$ are —N(H)—;

Y is O or S; and

W is optionally substitute heteroaryl. In one embodiment, W is heteroaryl containing at least two heteroatoms selected from the group consisting of N, O, and S, said heteroaryl ring optionally substituted with one to four substituents selected from the group consisting of optionally substituted $C_{1-6}$alkyl, aryl, N(R$^3$)$_2$, OR$^3$, C(O)N(R$^3$)$_2$, CO$_2$R$^3$, CN, and halo, wherein $R^3$ is as previously defined.

Other preferred compounds of structural formula (I) are those wherein W is selected from the group consisting of pyridazinyl, pyrimidinyl, pyrazinyl, and triazinyl, optionally substituted with one to four substituents selected from the group consisting of $C_{1-6}$alkyl, aryl, N(R$^3$)$_2$, C(O)N(R$^3$)$_2$, CO$_2$R$^3$, OR$^3$, and halo.

In some preferred embodiments, W is selected from the group consisting of

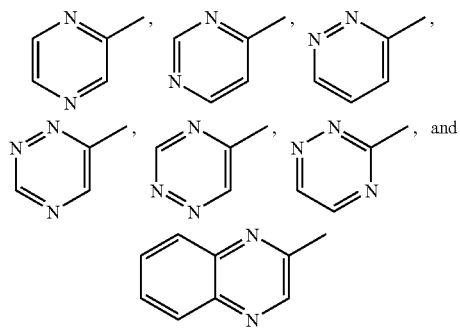

optionally substituted with one to four substituents selected from the group consisting of $C_{1-6}$alkyl, $C_{2-6}$-alkynyl, aryl, heteroaryl, CN, $CO_2R^3$, $N(R^3)_2$, $OR^3$, and halo.

In more preferred embodiments, W is

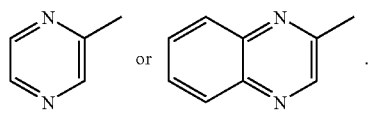

In a most preferred embodiment, W is pyrazinyl and $X^1$ and $X^2$ each are N(H).

In yet another preferred embodiment, $R^6$ is heteroaryl selected from the group consisting of

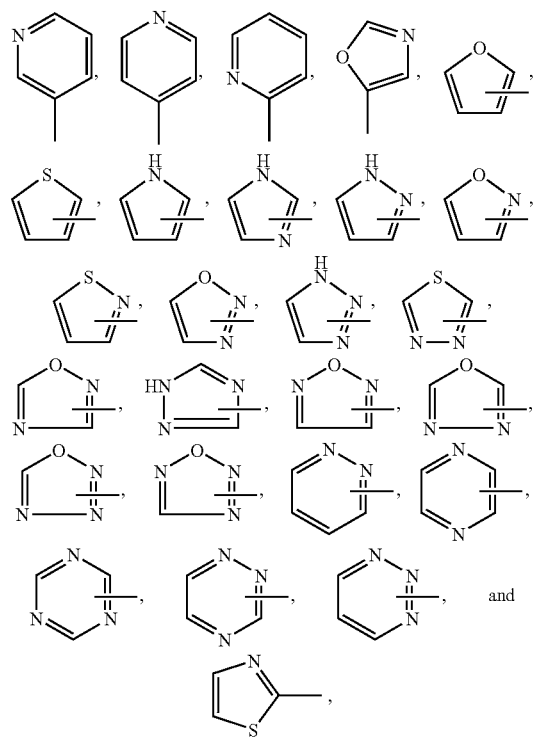

and optionally substituted with $C_{1-3}$alkyleneN($R^4$)$_2$.

As used herein, the term "alkyl" means straight chained and branched hydrocarbon groups containing the indicated number of carbon atoms, typically methyl, ethyl, and straight chain and branched propyl and butyl groups. Unless otherwise indicated, the hydrocarbon group can contain up to 20 carbon atoms. The term "alkyl" includes "bridged alkyl," i.e., a $C_6$-$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. Alkyl groups optionally can be substituted, for example, with hydroxy (OH), halo, aryl, heteroaryl, cycloalkyl, heterocycloalkyl, amino ($N(R^3)_2$), and sulfonyl ($SO_2R^3$), wherein $R^3$ is as previously defined.

The term "cycloalkyl" means a cyclic $C_{3-8}$hydrocarbon group, e.g., cyclopropyl, cyclobutyl, cyclohexyl, or cyclopentyl. "Heterocycloalkyl" is defined similarly as cycloalkyl, except the ring contains one to three heteroatoms independently selected from the group consisting of oxygen, nitrogen, and sulfur. Cycloalkyl and heterocycloalkyl groups can be saturated or partially unsaturated ring systems optionally substituted with, for example, one to three groups, independently selected from the group consisting of $C_{1-4}$alkyl, $C_{1-3}$alkyleneOH, $C(O)NH_2$, $NH_2$, oxo (=O), aryl, trifluoroethanoyl, and OH. Heterocycloalkyl groups optionally can be further N-substituted with $C_{1-6}$alkyl, hydroxy$C_{1-6}$alkyl, $C_{1-3}$alkylenearyl, or $C_{1-3}$alkyleneheteroaryl.

The term "alkenyl" defined identically as "alkyl," except the group contains a carbon-carbon double bond.

The term "alkynyl", is defined identically as "alkyl," except the group contains a carbon-carbon triple bond.

The term "alkylene" means an alkyl group having a substituent. For example, the term "$C_{1-6}$alkyleneC(O)OR" refers to an alkyl group containing one to six carbon atoms substituted with a —C(O)OR group. The alkylene group is optionally substituted with one or more substituent previously listed as an optional alkyl substituent.

The term "halo" or "halogen" means fluorine, bromine, chlorine, and iodine.

The term "aryl," alone or in combination, means a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, $C_{1-6}$alkyl, $C_{2-6}$alkenyl, $OCF_3$, $NO_2$, CN, NC, $N(R^3)_2$, $OR^3$, $CO_2R^3$, $C(O)N(R^3)_2$, $C(O)R^3$, $N(R^1)COR^3$, $N(R^1)C(O)OR^3$, $N(R^1)C(O)OR^3$, $N(R^1)C(O)C_{1-3}$alkyleneC(O)R^3$, $N(R^1)C(O)C_{1-3}$alkyleneC(O)OR^3$, $N(R^1)C(O)C_{1-3}$alkyleneOR^3$, $N(R^1)C(O)C_{1-3}$alkyleneNHC(O)OR^3$, $N(R^1)C(O)$—$C_{1-3}$alkyleneSO$_2$NR$^3$, $C_{1-3}$alkyleneOR$^1$, and SR$^3$, wherein $R^1$ and $R^3$ are as previously defined. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like. The terms "aryl$C_{1-3}$alkyl" and "heteroaryl$C_{1-3}$alkyl" mean an aryl or heteroaryl group having a $C_{1-3}$alkyl substituent.

The term "heteroaryl" means a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, $C_{1-6}$alkyl, aryl, heteroaryl, $CF_3$, CN, $C(O)N(R^3)_2$, $CO_2R^2$, $N(R^3)_2$, $OR^3$, and halo, wherein $R^3$ is as previously defined. Examples of heteroaryl groups include, but are not limited to, thienyl, furyl, pyridyl, oxazolyl, quinolyl, isoquinolyl, indolyl, triazinyl, triazolyl, isothiazolyl, isoxazolyl, imidizolyl, benzothiazolyl, pyrazinyl, pyrimidinyl, thiazolyl, and thiadiazolyl.

The term "hydro" is —H.
The term "hydroxy" is —OH.
The term "nitro" is —$NO_2$.
The term "cyano" is —CN.
The term "isocyano" is —NC.
The term "trifluoromethoxy" is —$OCF_3$.
The term "azido" is —$N_3$.
The term "3- to 8-membered ring" means carbocyclic and heterocyclic aliphatic or aromatic groups, including, but not limited to, morpholinyl, piperidinyl, phenyl, thiophenyl, furyl, pyrrolyl, imidazolyl, pyrimidinyl, and pyridinyl, optionally substituted with one or more, and in particular one to three, groups exemplified above for aryl groups.

The carbon atom content of hydrocarbon-containing moieties is indicated by a subscript designating the minimum and maximum number of carbon atoms in the moiety, e.g., "$C_{1-6}$ alkyl" refers to an alkyl group having one to six carbon atoms, inclusive.

In the structures herein, for a bond lacking a substituent, the substituent is methyl, for example,

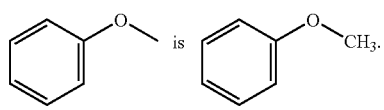

When no substituent is indicated as attached to a carbon atom on a ring, it is understood that the carbon atom contains the appropriate number of hydrogen atoms. In addition, when no substituent is indicated as attached to a carbonyl group or a nitrogen atom, for example, the substituent is understood to be hydrogen, e.g.,

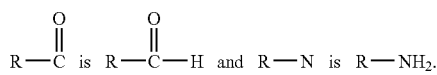

The abbreviation "Me" is methyl. The abbreviation CO and C(O) is carbonyl (C=O).

The notation $N(R^x)$ (wherein x represents an alpha or numeric character, such as for example $R^a$, $R^b$, $R^3$, $R^4$, and the like) is used to denote two $R^x$ groups attached to a common nitrogen atom. When used in such notation, the $R^x$ group can be the same or different, and are selected from the group as defined by the $R^x$ group.

DNA-damaging agents that activate cell cycle checkpoints generally are referred to herein as "checkpoint activators." DNA-damaging agents that activate the checkpoint designated "Chk1" (pronounced "check-one") are referred to herein as "Chk1 activators." Likewise, inhibitors of such checkpoints are referred to herein as "checkpoint inhibitors" and "Chk1 inhibitors," respectively.

As used herein, Chk1 inhibitors are compounds that are capable of at least partially abrogating cell cycle checkpoint activity of the Chk1 protein. Abrogation of cell cycle checkpoint is achieved when the cellular checkpoint mechanism is overcome sufficiently to allow the cell to pass from the cell cycle phase in which it is halted to the next phase in the cell cycle or to allow the cell to pass directly to cell death. Abrogation of the cell cycle checkpoint permits cells to carry damage or imperfections to subsequent cell cycle phases, thereby inducing or promoting cell death. Cell death can occur by any associated mechanism, including apoptosis and mitotic catastrophe. The compounds of the invention are Chk1 inhibitors.

Chk1 activator includes any known or after-discovered agent having the ability to activate Chk1 kinase activity, and thus induce at least partial cell cycle arrest. Chk1 activators include agents capable of arresting the cell cycle at any phase of the cell cycle, which phase may be referred to herein as the "target phase" for that activator. Target phases include any of the cell cycle phases except mitosis, i.e., the G1 phase, S phase, and G2 phase. Chk1 activators useful in the invention include DNA damaging agents, such as chemotherapeutic agents and/or radiation. Radiation Chk1 activators include, but are not limited to, ionizing radiation. Ionizing radiation includes electromagnetic or particulate radiation capable of producing ion pairs by interacting with matter. Ionizing radiation includes X and gamma rays, alpha and beta particles, neutrons, and charged nuclei. Radiation includes ultraviolet light, visible light, infrared radiation, microwave radiation, and mixtures thereof. Assays such as that described in Example 9 can be used to determine whether an agent is a Chk1 activator.

"Inhibiting aberrant cell proliferation" means retarding the rate at which aberrantly proliferating cells proliferate or eliminating such proliferation altogether. This inhibition can result either from a decreased rate of replication, an increased rate of cell death, or both. Cell death can occur by any mechanism, including apoptosis and mitotic catastrophe.

"Preventing aberrant cell proliferation" means inhibiting aberrant cell proliferation-prior to occurrence, or inhibiting the recurrence thereof.

"In vivo" means within a living subject, as within an animal or human. In this context, agents can be used therapeutically in vivo to retard or eliminate the proliferation of aberrantly replicating cells. The agents also can be used in vivo as a prophylactic to prevent aberrant cell proliferation or the manifestation of symptoms associated therewith.

"Ex vivo" means outside a living subject. Examples of ex vivo cell populations include cell cultures and biological samples, such as fluid or tissue samples from humans or animals. Such samples can be obtained by methods well known in the art. Exemplary biological fluid samples include blood, cerebrospinal fluid, urine, and saliva. Exemplary tissue samples include tumors and biopsies thereof. In this context, the present compounds can be in numerous applications, both therapeutic and experimental.

"Radiosensitizer" means a compound administered to a human or other animal in a therapeutically effective amount to increase the sensitivity of cells to electromagnetic radiation and/or to promote the treatment of diseases treatable with electromagnetic radiation.

"Radiation" includes, but is not limited to, radiation having the wavelength of $10^{-20}$ to 100 meters.

The term "container" means any receptacle and closure therefor suitable for storing, shipping, dispensing, and/or handling a pharmaceutical product.

The term "package insert" means information accompanying the product that provides a description of how to administer the product, along with the safety and efficacy data required to allow the physician, pharmacist, and patient to make an informed decision regarding use of the product. The package insert generally is regarded as the "label" for a pharmaceutical product.

The present invention includes all possible stereoisomers and geometric isomers of the compounds of structural formula (I). The present invention includes not only racemic compounds, but optically active isomers as well. When a compound of structural formula (I) is desired as a single enantiomer, it can be obtained either by resolution of the final product or by stereospecific synthesis from either an isomerically pure starting material or use of a chiral auxiliary reagent, for example, see Ma et al., *Tetrahedron: Asymmetry,* 8(6), pages 883-88, 1997. Resolution of the final product, an intermediate, or a starting material can be achieved by any suitable method known in the art. Additionally, in situations where tautomers of the compounds of structural formula (I) are possible, the present invention is intended to include all tautomeric forms of the compounds. As demonstrated hereafter, specific stereoisomers can exhibit an exceptional ability to inhibit Chk1 in combination with chemotherapeutic or radiotherapeutic treatments.

Prodrugs of compounds of structural formula (I) also can be used as the compound in a method of the present invention. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, 1985; Silverman, "The Organic Chemistry of Drug Design and Drug Action," Academic Press, San Diego, chapter 8, 1992; Hiligren et al., *Med. Res. Rev.,* 15, 83, 1995).

Compounds of the present invention can contain one or more functional groups. The functional groups, if desired or necessary, can be modified to provide a prodrug. Suitable prodrugs include, for example, acid derivatives, such as amides and esters. It also is appreciated by those skilled in the art that N-oxides can be used as prodrugs.

Compounds of the invention can exist as salts. Pharmaceutically acceptable salts of the compounds of the invention generally are preferred in the methods of the invention. As used herein, the term "pharmaceutically acceptable salts" refers to salts or zwitterionic forms of the compounds of structural formula (I). Salts of compounds of formula (I) can be prepared during the final isolation and purification of the compounds or separately by reacting the compound with an acid having a suitable cation. Suitable pharmaceutically acceptable cations include alkali metal (e.g., sodium or potassium) and alkaline earth metal (e.g., calcium or magnesium) cations. In addition, the pharmaceutically acceptable salts of compounds of structural formula (I) that contain a basic center are acid addition salts formed with pharmaceutically acceptable acids. Examples of acids which can be employed to form pharmaceutically acceptable salts include inorganic acids such as hydrochloric, hydrobromic, sulfuric, and phosphoric, and organic acids such as oxalic, maleic, succinic, malonic, and citric. Nonlimiting examples of salts of compounds of the invention include, but are not limited to, hydrochloride, hydrobromide, hydroiodide, sulfate, bisulfate, 2-hydroxyethanesulfonate, phosphate, hydrogen phosphate, acetate, adipate, alginate, aspartate, benzoate, butyrate, camphorate, camphorsulfonate, citrate, digluconate, glycerolphosphate, hemisulfate, heptanoate, hexanoate, formate, succinate, malonate, fumarate, maleate, methanesulfonate, mesitylenesulfonate, naphthylenesulfonate, nicotinate, oxalate, pamoate, pectinate, persulfate, 3-phenylpropionate, picrate, pivalate, propionate, trichloroacetate, trifluoroacetate, glutamate, bicarbonate, undecanoate, lactate, citrate, tartrate, gluconate, benzene sulphonate, and p-toluenesulphonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include compounds of structural formula (I) as well as pharmaceutically acceptable salts, solvates, or prodrugs thereof.

The compounds of the present invention can be therapeutically administered as the neat chemical, but it may be useful to administer the compounds as a pharmaceutical composition or formulation. Thus, the present invention provides a pharmaceutical composition comprising a compound of formula (I) together with a pharmaceutically acceptable diluent or carrier therefor. Also provided is a process of preparing a pharmaceutical composition comprising admixing a compound of formula (I) with a pharmaceutically acceptable diluent or carrier therefor.

Accordingly, the present invention further provides pharmaceutical formulations comprising a compound of structural formula (I), or a pharmaceutically acceptable salt, prodrug, or solvate thereof, together with one or more pharmaceutically acceptable carriers' and, optionally, other therapeutic and/or prophylactic ingredients. The carriers are "acceptable" in the sense of being compatible with the other ingredients of the formulation and not deleterious to the recipient thereof. Such carriers may be found for example, in *Remington's Pharmaceutical Sciences,* $17^{th}$ Ed., Mack Publishing Co., Easton, Pa. (1985).

Compounds of the invention exhibit good potency against Chk1. Potency typically is expressed as the concentration of a compound required to achieve a certain result. The greater the potency, the less compound required to perform its intended function. In vitro potency typically is expressed in terms of $IC_{50}$ values and measured using a dose-response assay. $IC_{50}$ values can be measured by contacting a sensitive assay system with a compound of interest over a range of concentrations, including concentrations at which no or minimal effect is observed, through higher concentrations at which partial effect is observed, to saturating concentrations at which a maximum effect is observed. Theoretically, such assays of the dose-response effect of inhibitor compounds can be described as a sigmoidal curve expressing a degree of inhibition as a function of concentration when plotted on a log scale. The curve also theoretically passes through a point at which the concentration is sufficient to reduce activity of the checkpoint enzyme to a level that is 50% that of the difference between minimal and maximal enzyme activity observed in the assay. This concentration is defined as the Inhibitory Concentration at 50% inhibition or $IC_{50}$ value.

$IC_{50}$ values can be determined using conventional biochemical (acellular) assay techniques or cell-based assay techniques well known to those of ordinary skill in the art. An example of such an assay is provided in Example 1 below.

Preferably, $IC_{50}$ values are obtained by performing the relevant assay at least twice, with the $IC_{50}$ value expressed as the average (arithmetic mean, or "mean") of the individual values obtained. More preferably, the assay is repeated from 3 to 10 (or more) times, with the $IC_{50}$ value expressed as the mean of the values obtained. Most preferably, the assay is performed a number of times sufficient to generated a statistically reliable mean $IC_{50}$ value, using statistical methods known to those of ordinary skill in the art.

Compounds of the invention, when assayed as described in Example 1 below, exhibit $IC_{50}$ values of less than about 5 µM, and down to about 0.1 nM. In some embodiments compounds demonstrate an $IC_{50}$ value of about 550 nM or less, in other embodiments less than about 250 nM, in others less than about 200 nM, in others less than about 150 nM, in others less than about 100 nM, in others less than about 75 nM, in others less than about 50 nM, and in others less than about 25 nM. In preferred embodiment, compounds of the invention exhibit selectivity for inhibiting Chk1 over other protein kinases. Selectivity may be advantageous in reducing adverse side effects and/or increasing therapeutic index.

"Selectivity" is expressed herein as "fold selectivity." In general, fold selectivity, as used herein, is the $IC_{50}$ of a test compound for a comparison enzyme divided by the $IC_{50}$ of a comparator enzyme. In particular, fold selectivity for a Chk1 inhibitor, as used herein, is the $IC_{50}$ of a Chk1 inhibitor (a test compound) for Chk1 (the comparison enzyme) divided by the $IC_{50}$ for a comparator enzyme. Comparator enzymes against which compounds of the invention may be measured include at least the following protein kinases: Cdc2, Chk2, CTAK, EphA1, EphA2, Erk1, FGFR1, FGFR4, IR, JNK1, c-Kit, p38alpha, p38beta, p38delta, Ros, Rse, Rsk2, TrkA, TrkB, protein kinase A, protein kinase C, pp60v-src, protein kinase B/Akt-1, p38MapK, p70S6K, calcium calmodulin-dependent kinase II, and ab1 tyrosine kinase. Assays for determining $IC_{50}$ values for a test compound against a comparator enzyme are described in Example 2 and are well known to those of ordinary skill in the art. Preferred compounds of the invention exhibit at least about 20-fold selectivity over the aforementioned protein kinases tested.

Compounds and pharmaceutical-compositions suitable for use in the present invention include those wherein the active ingredient is administered in an effective amount to achieve its intended purpose. More specifically, a "therapeutically effective amount" means an amount sufficient to treat an individual suffering an indication, or to alleviate the existing symptoms of the indication. Determination of a therapeutically effective amount is well within the capability of those skilled in the art, especially in light of the detailed disclosure provided herein.

In addition to the Chk1 inhibitor, pharmaceutical compositions of the invention can be formulated to include cytokines, lymphokines, growth factors, other hematopoietic factors, or mixtures thereof, to reduce adverse side effects that can arise from, or be associated with, administration of the pharmaceutical composition alone. Alternatively, such biologically active agents may be included in a pharmaceutical composition of the invention to promote a desired therapeutic effect. Adjuvant biologically active pharmaceutical compositions useful in pharmaceutical compositions of the invention include, but are not limited to, M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNF, G-CSF, Meg-CSF, GM-CSF, thrombopoietin, stem cell factor, erythropoietin, angiopoietins, including Ang-1, Ang-2, Ang-4, Ang-Y, and/or the human angiopoietin-like polypeptide, vascular endothelial growth factor (VEGF), angiogenin, bone morphogenic protein-1 (BMP-1), BMP-2, BMP-3, BMP-4, BMP-5, BMP-6, BMP-7, BMP-8, BMP-9, BMP-10, BMP-11, BMP-12, BMP-13, BMP-14, BMP-15, BMP receptor IA, BMP receptor IB, brain derived neurotrophic factor, ciliary neutrophic factor, ciliary neutrophic factor receptor cytokine-induced neutrophil chemotactic factor 1, cytokine-induced neutrophil chemotactic factor 2, endothelial cell growth factor, endothelin 1, epidermal growth factor, epithelial-derived neutrophil attractant, fibroblast growth factor (FGF) 4, FGF 5, FGF 6, FGF 7, FGF 8, FGF 8b, FGF 8c, FGF 9, FGF 10, FGF acidic, FGF basic, glial cell line-derived neutrophic factor receptor 1, glial cell line-derived neutrophic factor receptor 2, growth related protein, growth related protein, growth related protein, growth related protein, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor, platelet derived growth factor receptor, pre-B cell growth stimulating factor, stem cell factor, stem cell factor receptor, transforming growth factor (TGF), TGF, TGF 1, TGF 1.2, TGF 2, TGF 3, TGF 5, latent TGF 1, TGF, binding protein I, TGF binding protein II, TGF binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

The compounds of structural formula (I) also can be conjugated or linked to auxiliary moieties that promote a beneficial property of the compound in a method of therapeutic use. Such conjugates can enhance delivery of the compounds to a particular anatomical site or region of interest (e.g., a tumor), enable sustained therapeutic concentrations of the compounds in target cells, alter pharmacokinetic and pharmacodynamic properties of the compounds, and/or improve the therapeutic index or safety profile of the compounds. Suitable auxiliary moieties include, for example, amino acids, oligopeptides, or polypeptides, e.g., antibodies such as monoclonal antibodies and other engineered antibodies; and natural or synthetic ligands to receptors in target cells or tissues. Other suitable auxiliaries include fatty acid or lipid moieties that promote biodistribution and/or uptake of the compound by target cells (see, e.g., Bradley et al., *Clin. Cancer Res.*, 7:3229, 2001).

Formulations of the present invention can be administered in a standard manner for the treatment of the indicated diseases, such as by oral, parenteral, transmucosal (e.g., sublingual or via buccal administration), topical, transdermal, rectal, or inhalation (e.g., nasal or deep lung inhalation) administration. Parenteral administration includes, but is not limited to intravenous, intraarterial, intraperitoneal, subcutaneous, intramuscular, intrathecal, and intraarticular modes of administration. Parenteral administration also can be accomplished using a high pressure technique, like POWDERJECT™ (Powderject Pharmaceuticals PLC, Oxford, England).

For oral administration and buccal administration, the composition can be in the form of tablets or lozenges formulated in conventional manner. For example, tablets and capsules for oral administration can contain conventional excipients such as binding agents (for example, syrup, acacia, gelatin, sorbitol, tragacanth, mucilage of starch, or polyvinylpyrrolidone), fillers (for example, lactose, sugar, microcrystalline cellulose, maize-starch, calcium phosphate, or sorbitol), lubricants (for example, magnesium stearate, stearic acid, talc, polyethylene glycol or silica), disintegrants (for example, potato starch or sodium starch glycolate), or wetting agents (for example, sodium lauryl sulfate). The tablets can be coated according to methods well known in the art.

Alternatively, compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, for example suspending agents, such as sorbitol syrup, methylcellulose, glucose/sugar syrup, gelatin, hydroxyethylcellulose, hydroxypropylmethylcellulose, carboxymethylcellulose, aluminum stearate gel, and hydrogenated edible fats; emulsifying agents, such as lecithin, sorbitan monooleate, or acacia; nonaqueous vehicles (which can include edible-oils), such as almond oil, fractionated coconut oil, oily esters, propylene glycol, and ethyl alcohol; and preservatives, such as methyl or propyl p-hydroxybenzoate and sorbic acid.

Such preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Topical and transdermal formulations comprise conventional aqueous or nonaqueous vehicles, such as eye drops, creams, ointments, lotions, and pastes, or are in the form of a medicated plaster, patch, or membrane.

Additionally, compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, pyrogen-free water) before use.

A composition of the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (e.g., an emulsion in an acceptable oil), ion exchange resins, or as sparingly soluble., derivatives (e.g., a sparingly soluble salt).

For veterinary use, a compound of formula (I), or a pharmaceutically acceptable salt, prodrug, or solvent thereof, is administered as a suitably acceptable formulation in accordance with normal veterinary practice. The veterinarian can readily determine the dosing regimen and route of administration that is most appropriate for a particular animal. Animals treatable by the present compounds and methods include, but are not limited to, pets, livestock, show animals, and zoo specimens.

Synthetic Methods

Compounds of the present invention can be pre-pared by the following synthetic schemes. Starting materials can be obtained from commercial sources or prepared by well-established literature methods known to those of ordinary skill in the art. The groups X, $R^1$, $R^3$, $R^4$, $R^5$, $R^6$, $R^7$, $R^8$, $R^9$ and $R^{10}$ are defined above unless otherwise noted below.

Scheme 1

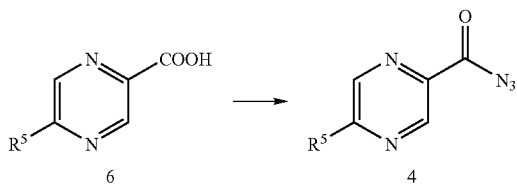

As illustrated in Scheme 1, compounds of formula 4 can be prepared from compounds of formula 6 by treatment with a base, such as DIEA, and diphenyl phosphoryl azide. A typical solvent for this reaction is THF, and the reaction is performed behind a blast shield at room temperature over a one to twelve hour period Scheme 2

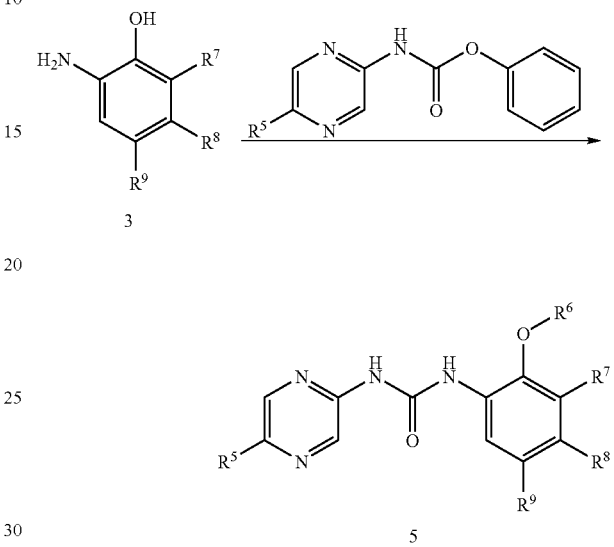

Scheme 2 shows an alternative synthesis of compounds of formula 5. Compounds of formula 3 are treated with compounds of formula 7, which is prepared according to Scheme 4. A useful, nonlimiting solvent is DMF, and the reaction temperature is maintained between room temperature and 60° C. for about one to twelve hours.

Scheme 3

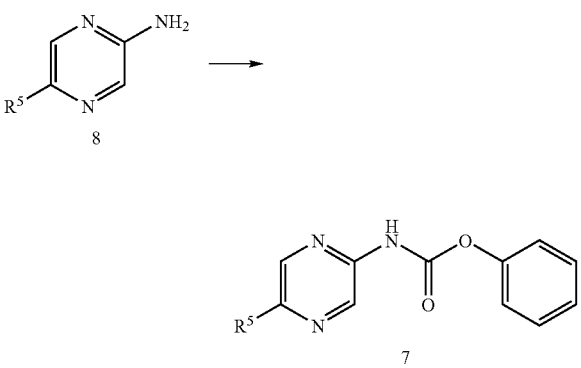

As demonstrated in Scheme 3, compounds of formula 7 can be prepared from compounds of formula 8 by treatment with an aryl chloroformate, such as phenyl chloroformate or p-nitrophenyl chloroformate, in the presence of a base, such as pyridine. Nonlimiting solvents used in this reaction include $CH_2Cl_2$ or pyridine, at temperatures from 0° C. to room temperature.

Scheme 4

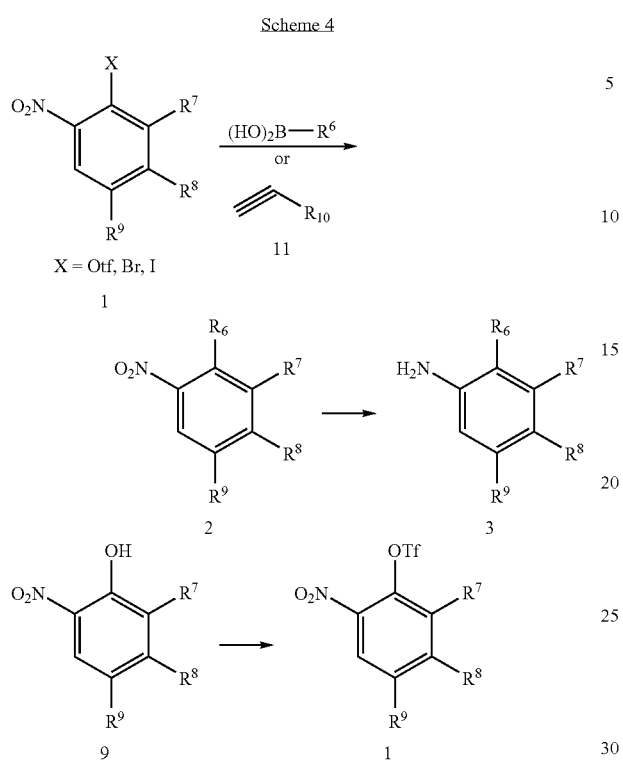

Scheme 4 shows an approach to compounds of formula 3. Compounds of formula 1 are converted to compounds of formula 2 by treatment with aryl boronic acids and a source of palladium(0) (for example, palladium tetrakis triphenylphosphine) in the presence of a basic aqueous solution, such as Na$_2$CO$_3$, K$_2$CO$_3$, or K$_3$PO$_4$. Nonlimiting examples of solvents used in this reaction include THF, dioxane, or ethylene glycol dimethyl ether. The reaction typically is performed at temperatures between 0° C. and 90° C. for about 1 to 12 h. Compounds of formula 2 are converted to compounds of formula 3 in the presence of Pd/C, Pt/C, or zinc, for example. Examples of solvents used in this reaction include, but are not limited to, MeOH, EtOH, or HOAc. Alternatively, compounds of formula 1 can be used to arylate terminal alkynes, 11, using a catalyst, such as PdCl$_2$(PPH$_3$)$_2$ or any other source of palladium(0). Reactions typically are conducted at temperatures varying from room temperature to 90° C., in the presence of a base, such as triethylamine.

Furthermore, compounds of formula 1, where X is a triflate, i.e., tf, can be obtained from compounds of formula 9. Typical reagents include triflic anhydride or N-phenyl triflimide. The reaction typically is performed at temperatures between −10° C. and room temperature. A nonlimiting example of a solvent is dichloromethane. Nonlimiting examples of bases are TEA or diisopropyl ethyl amine.

Scheme 6

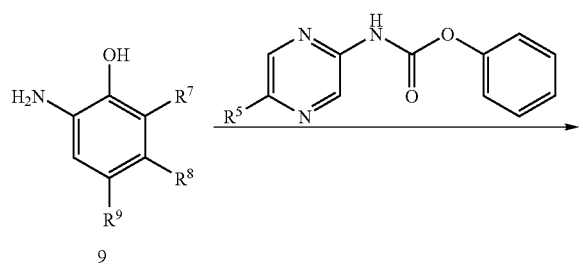

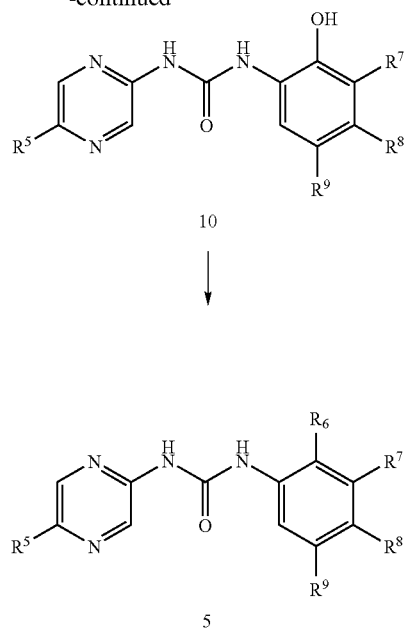

Scheme 6 illustrates an alternative synthesis for compounds of formula 5. Compounds of formula 3 can be converted to compounds of formula 10 following procedures described in Scheme 2. Compounds of formula 10 then can be converted to compounds of formula 5 following procedures described in Scheme 4.

Nonlimiting examples of compounds of structural formula (I) are provided below, the synthesis of which were performed in accordance with the general procedures set forth below and in copending U.S. Patent Application Publication No. 2003/0069284, incorporated herein by reference. Additional compounds of the invention can be prepared using the above general schemes, and the following specific syntheses, by a judicious solution of starting materials.

Abbreviations used in the syntheses described herein are: hours (h), minutes (min), atmosphere (atm), deionized (DI), nitrogen (N$_2$), water (H$_2$O), magnesium sulfate (MgSO$_4$), hydrochloric acid (HCl), dimethyl sulfoxide (DMSO), diisopropyl azodicarboxylate (DIAD), dichloro palladium bis triphenylphosphene (PdCl$_2$(PPh$_3$)$_2$), triethylamine (TEA), carbon dioxide (CO$_2$), methylene chloride (CH$_2$Cl$_2$), chloroform (CHCl$_3$), methanol (MeOH), ammonium hydroxide (NH$_4$OH), ammonium chloride (NH$_4$Cl), deuterated chloroform (CDCl$_3$), tetrahydrofuran (THF), N-methylpyrrolidone (NMP), acetic acid (HOAc), sodium hydroxide (NaOH), ethyl acetate (EtOAc), ethanol (EtOH), dimethyl sulfoxide (DMSO), diethyl ether (Et$_2$O), p-toluene sulfonic acid (p-TsOH), sodium carbonate (Na$_2$CO$_3$), sodium bicarbonate. (NaHCO$_3$), nitric acid (HNO$_3$), sodium chloride (NaCl), saturated (sat'd), thin layer chromatography (TLC), potassium carbonate (K$_2$CO$_3$), potassium phosphate (K$_3$PO$_4$), palladium on carbon (Pd/C), potassium chloride (KCl), phosphate buffered saline (PBS), cuprous iodide (Cu(1)I), sodium sulfate (Na$_2$SO$_4$), dimethylformamide (DMF), 1,8-diazabicyclo[5.4.0]undec-7-ene (DBU), and N,N-diisopropylethylamine (DIEA).

Intermediate 1:

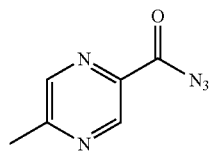

5-Methyl-pyrazine-2-carbonyl azide

To a stirred suspension of 5-methyl-pyrazine-2-carboxylic acid (25 g, 181 mmol) in 540 mL THF at room temperature under N₂ was added DIEA (31.7 mL, 181 mmol) resulting in a brown solution. Diphenyl phosphoryl azide (39.2 mL, 181 mmol) then was added dropwise as a solution in 50 mL THF over 1 h behind a blast shield. The reaction was allowed to stir overnight. The reaction then was rotary evaporated to a small volume at room temperature and partitioned between Et₂O (1 L) and H₂O (1 L). The H₂O layer was back extracted with 2×250 mL Et₂O, and the combined organics washed 2×1 L with sat'd Na₂CO₂. The organics were dried (MgSO₄), filtered, and concentrated to a solid mass, which was triturated with Et₂O to give the product as a yellow solid (15 g, 50%). Purer compound could be isolated by taking xg of the crude product in 20×mL of Et₂O, and treating with 1-2×g of decolorizing carbon at room temperature for a few minutes. After filtration and concentration, this material was homogeneous by TLC in EtOAc and pure white. The recovery was typically 65%.

Compound 1:

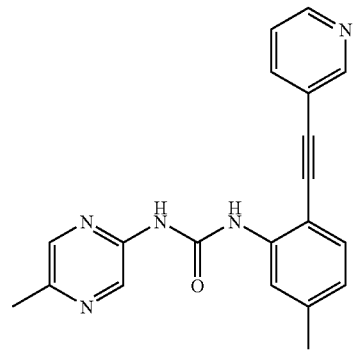

1-(s-Methyl-pyrazin-2-yl)-3-(5-methyl-2-pyridin-3-ylethynyl-phenyl)-urea

Step 1. tert-Butyl-dimethyl-(4-methyl-2-nitrophenylethynyl)-silane

To a stirred solution of 1-bromo-4-methyl-2-nitro-benzene (3.24 g, 15.0 mmol), PdCl₂(PPh₃)₂ (1.05 g, 1.5 mmol), and Cu(1)I (5.7 g, 30 mmol) was added TEA (40 mL) followed by TMS-acetylene (5.3 mL, 37.5 mmol). After stirring at 60° C. for 12 h, the reaction was filtered, diluted with EtOAc (150 mL) and 10% Na₂CO₃ (150 mL). The organic layer was washed with brine, dried over MgSO₄, filtered, and dried under reduced pressure to yield 4.0 g of an amorphous black residue. Step 2. 1-Ethynyl-4-methyl-2-nitro-benzene To a stirred solution of tert-butyl-dimethyl-(4-methyl-2-nitro-phenylethynyl)-silane (3.5 g, 15 mmol) in MeOH (20 mL) was added NaOH (1.8 g, 45 mmol, in 5 mL of H₂O). After stirring for 1 hour, the reaction was diluted with EtOAc (150 mL) and 10% Na₂CO₃ (150 mL). The layers were separated and the aqueous layer was extracted with EtOAc (1 by 75 mL) The organic layers were combined, dried over MgSO₄, filtered, and dried under reduced pressure to yield 1.40 g (58% over two steps) of a brown solid.

Step 3. 3-(4-Methyl-2-nitro-phenylethynyl)-pyridine

To a stirred solution of 3-bromopyridine (608 mg, 3.85 mmol), PdCl₂(PPh₃)₂ (246 mg, 0.35 mmol), and Cu(1)I (733 mg, 3.85 mmol) was added TEA (10 mL) followed by 1-ethynyl-4-methyl-2-nitro-benzene (564 mg, 3.5 mmol). After stirring at 60° C. for 4 h, the reaction was filtered, and diluted with EtOAc (150 mL) and 10% Na₂CO₃ (150 mL). The organic layer was washed with brine, dried over MgSO₄; filtered, and dried under reduced pressure. The material was purified using a Biotage 40M cartridge eluting with hexanes/EtOAc (7/3) to yield a light brown oil.

Step 4. 5-Methyl-2-pyridin-3-ylethynyl-phenylamine

To a solution of 3-(4-methyl-2-nitro-phenylethynyl)-pyridine (1 mmol) in MeOH (1 mL) was added 0.5 mL sat'd NH₄Cl followed by zinc dust (0.33 g, 5.0 mmol). The mixture was stirred for 10 min, then diluted with EtOAc (50 mL) and Na₂CO₃ (50 mL of 10% aqueous solution). The organic layer was dried over MgSO₄, filtered, and concentrated under reduced pressure to yield the desired material as a clear oil.

Step 5. 1-(5-Methyl-pyrazin-2-yl)-3-(5-methyl-2-pyridin-3-ylethynyl-phenyl)-urea To a stirred solution of 5-methyl-pyrazine-2-carbonyl azide (compound 7) (163 mg, 1.0 mmol) in toluene (4 ml) and previously heated to 90° C. for 15 min, was added 5-methyl-2-pyridin-3-ylethynyl-phenylamine (1 mmol). The mixture was cooled to 65° C. and stirred for 12 h. The reaction mixture then was cooled to room temperature. Ethyl acetate was added to the organic layer, and washed with brine, dried over MgSO₄. After filtration, and evaporation under reduced pressure, an oil was isolated and purified on column chromatography (silica gel) eluted with EtOAc/hexanes 1:4. ¹H-NMR (400 MHz, CDCl₃) δ 11.39 (br s, 1H), .8.79 (s, 1H), 8.61 (d, 1H), 8.25 (s, 1H), 8.19 (s, 1H), 8.15 (s, 1H), 7.79 (d, 1H), 7.41 (m, 2H), 7.31 (m, 1H), 6.91 (d, 1H), 2.41 (s, 3H), 2.37 (s, 3H). LRMS (apci, positive) m/e 344.4 (M+1).

Compound 2

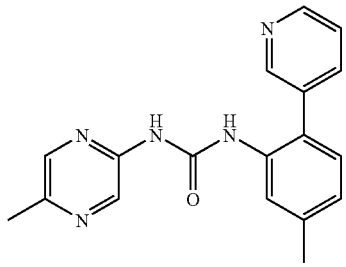

1-(5-Methyl-pyrazin-2-yl)-3-(5-methyl-2-pyridin-3-yl-phenyl)-urea

Step 1. 3-(4-Methyl-2-nitro-phenyl)-pyridine

4-Bromo-2-nitro-phenol (648 mg, 3.0 mmol) and 3-pyridyl boronic acid (387 mg, 3.15 mmol) were diluted with 5 mL of dioxane and placed under N$_2$. Potassium carbonate was diluted in 1 mL of H$_2$O and added to the reaction mixture. Tetrakis(triphenylphosphine) palladium (173 mg, 0.15 mmol) was added, then the reaction was heated to 70° C. and stirred overnight. The reaction was allowed to cool to room temperature, then diluted with 30 mL of EtOAc and 30 mL of 10% Na$_2$CO$_3$. The organic layer was washed with brine, dried over MgSO$_4$, filtered, and concentrated under reduced pressure. The material was purified with a Biotage 40M cartridge eluting with hexanes/EtOAc, 1/1 to yield an off white solid.

Step 2. 5-Methyl-2-pyridin-3-yl-phenylamine

Prepared according to compound 1, Step 4 from 3-(4-methyl-2-nitro-phenyl)-pyridine.

Step 3. 1-(5-Methyl-pyrazin-2-yl)-3-(5-methyl-2-pyridin-3-yl-phenyl)-urea

Prepared according to compound 1, Step 5 using 5-methyl-2-pyridin-3-yl-phenylamine and compound 7. $^1$H-NMR (400 MHz, CDCl$_3$) δ 11.00 (br s, 1H), 9.00 (s, 1H) 8.75 (s, 1H), 8.70 (d, 1H), 8.40 (s, 2H), 7.75 (d, 1H), 7.40 (m, 2H), 7.15 (d, 1H), 7.05 (d, 1H), 2.45 (s, 3H), 2.40 (s, 3H). LRMS (apci, positive) m/e 320.3 (M+1).

Compound 3

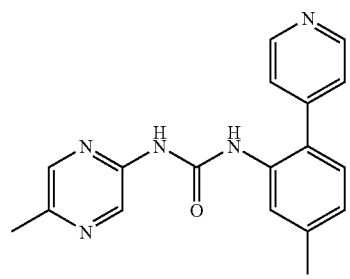

1-(5-Methyl-pyrazin-2-yl)-3-(5-methyl-2-pyridin-4-yl-phenyl)-urea

Step 1. 4-(4-Methyl-2-nitro-phenyl)-pyridine

Prepared according to Compound 2, Step 1 using 4-pyridyl boronic acid and 4-bromo-2-nitro-phenol.

Step 2. 5-Methyl-2-pyridin-4-yl-phenylamine

Prepared according to compound 1, Step 4 using 4-(4-methyl-2-nitro-phenyl)-pyridine.

Step 3. 1-(5-Methyl-pyrazin-2-yl)-3-(5-methyl-2-pyridin-4-yl-phenyl)-urea

Prepared according to compound 1, Step 5 using 5-methyl-2-pyridin-4-yl-phenylamine and compound 7. $^1$H-NMR (400 MHz, CDCl$_3$) δ 10.90 (br s, 1H), 8.65 (d, 2H), 8.25 (s, 1H), 8.20 (s, 1H), 8.10 (br s, 1H), 7.45 (d, 2H), 7.33 (s, 1H), 7.15 (d, 1H), 7.05 (d, 1H), 2.48 (s, 3H), 2.46 (s, 3H). LRMS (apci, positive) m/e 320.0 (M+1).

Compound 4:

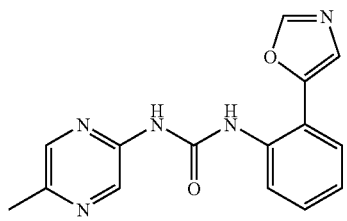

1-(5-Methyl-pyrazin-2-yl)-3-(2-oxazol-5-yl-phenyl)-urea

Step 1: 2-Oxazol-5-yl-phenylamine

2-Oxazol-5-yl-phenyl nitro (190 mgs, 1 mmol) was dissolved in 3 mL of EtOH at room temperature. A catalytic amount of Pearlman's catalyst was added and the hydrogenation was performed under 1 atm. After filtration over celite, the solution was evaporated under reduced pressure. A yellow solid was isolated.

Step 2: 1-(5-Methyl-pyrazin-1-yl)-3-(2-oxazol-5-yl-phenyl)-urea

Prepared according to compound 1, Step 5 using 2-oxazol-5-yl-phenylamine and compound 7. LRMS (apci, positive) m/e 296.0 (M+1).

Compound 5:

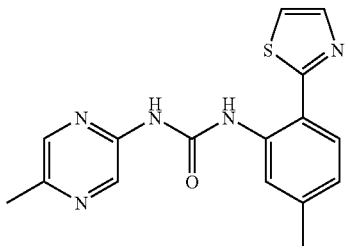

1-(5-Methyl-pyrazin-2-yl)-3-(5-methyl-2-thiazol-2-yl-phenyl)urea

Step 1: 4-Methyl-2-nitro-benzamide

4-Methyl-2-nitro benzamide was obtained from 4-methyl-2-nitro benzoic acid by the procedure described in *J. Am. Chem. Soc,* 79:1389 (1957).

Step 2: 4-Methyl-2-nitro-thio benzamide

4-Methyl-2-nitro benzamide (180 mgs, 1 mmol) and Belleu's reagent (529 mgs, 1 mmol) were dissolved in 3 mL of THF under N$_2$. The suspension was stirred overnight. A yellow solution had formed. The solution was concentrated, redissolved in 20 mL of CH$_2$Cl$_2$ and fresh grade silica gel was added. The solution was evaporated under reduced pressure, and the silica gel/absorbed compound were loaded into a Biotage ZIF unit. The compound was chromatographed on a Biotage 12M column with EtOAc:hexanes 3:7. The desired fractions were pooled and concentrated to give the desired material as a dark yellow solid.

Step 3: 2-(4-Methyl-2-nitro-phenyl-thiazole)

4-Methyl-2-nitro-thio benzamide (37 mg, 0.18 mmol) was dissolved in HOAc (5 mL) with pTsOH (90 mg, 0.047 mmol) and 2-bromo-1,1-diethoxy ethane (48 mg, 0.24 mmol). The mixture was heated to 100° C. for 1.5 hr. The desired product was isolated using the procedure described in *Chem. Pharm. Bull.*, 39(9):2323-2332 (1991).

Step 4: 2-(4-Methyl-2-amino-phenyl-thiazole)

2-(4-Methyl-2-nitro-phenyl-thiazole) (30 mgs, 0.13 mmol) was dissolved in EtOH (3 mL) with a catalytic amount of Pearlman's catalyst. The procedure described for compound 4, Step 1 was followed. The desired material was obtained in good yields.

Step 5: 1-(5-Methyl-pyrazin-2-yl)-3-(5-methyl-2-thiazol-2-yl-phenyl)urea

Prepared according to compound 1, Step 5 using 2-(4-methyl-2-amino-phenyl-thiazole) and compound 7. LRMS (apci, positive) in/e 326.0 (M+1).

Compound 6:

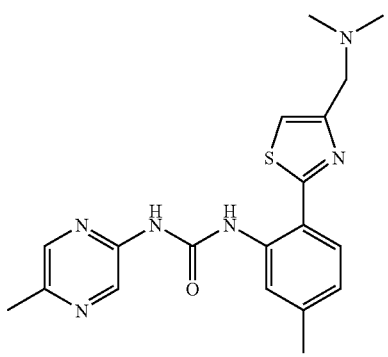

1-[2-(4-Dimethylaminomethyl-thiazol-2-yl)-5-methyl-phenyl]-3-(5-methyl-pyrazin-2-yl)-urea Step 1: 2-(4-Methyl-2-nitro-phenyl-thiazole-4-carboxylic acid ethyl ester 4-Methyl-2-nitro-thio benzamide (60 mgs, 0.30 mmol, prepared as described in compound 5, Step 2, was stirred in 1 mL absolute EtOH at room temperature under $N_2$. Ethyl bromo pyruvate (65 mgs, 0.33 mmol) was added, and the resulting solution was heated to 70° C. for 3 h. The reaction was diluted to 30 mL with EtOAc and washed with saturated $NaHCO_3$, and saturated NaCl. The organic layer was dried over $MgSO_4$, filtered and concentrated to a yellow oil, which was used as is in the next step.

Step 2: 2-(4-Methyl-2-nitro phenyl)thiazol-4-yl methanol 2-(4-Methyl-2-nitro-phenyl-thiazole-4-carboxylic acid ethyl ester (292 mg, 1 mmol) was dissolved in 5 mL of absolute EtOH at room temperature in an open flask. Sodium borohydride (1 mmol, 38 mg) was added portionwise over several hours and the reaction was monitored by TLC (EtOAc:hexanes 2:3). After completion of the reaction, 2N HCl was added carefully with stirring. After 15 min, the clear yellow solution was concentrated on the rotavap, and the crude mixture was partitioned between EtOAc (60 mL) and water (60 mL). The organics were isolated and washed with sat $NaHCO_3$ and 60 mL of sat NaCl. The organics were dried over $MgSO_4$, filtered and concentrated to provide an orange solid as the desired material.

Step 3: 2-(4-Methyl-2-nitro-phenyl)thiazole-4-carbaldehyde 2-(4-Methyl-2-nitro phenyl)thiazol-4-yl methanol (297 mg, 1.18 mmol) was stirred in 5 mL of $CH_2Cl_2$ at room temperature under $N_2$. The Dess-Martin reagent (500 mg, 1.18 mmol) was added as a solid. After 30 minutes, the reaction was complete. The reaction was diluted to 60 mL of $CH_2Cl_2$ and washed with 60 mL of 1N NaOH. The organics were dried over $MgSO_4$, filtered and concentrated under reduced pressure. The crude material was purified on a biotage column 12M eluted with EtOAc/hexanes 1:4 to give the desired material.

Step 4: Dimethyl-[2-(4-methyl-2-nitro-phenyl)thiazol-4-ylmethyl]amine

Dimethylamine (640 uL of a 2M solution in MeOH), sodium acetate, and sodium cyanoborohydride (56 mgs, 0.89 mmol) were stirred in 2.6 mL MeOH at room temperature under $N_2$. Glacial HOAc was added to adjust the pH to 7-8. 2-(4-Methyl-2-nitro-phenyl)thiazole-4-carbaldehyde (159 mgs, 0.64 mmol) then was added as a solution in 3.2 mL of MeOH. After 2 h, product formation was apparent by mass spectroscopy. The reaction was allowed to proceed overnight. At that time, acetone (500 uL) was added to quench any unreacted borohydride and the reaction acidified to pH<3. The reaction was concentrated. The residue was partitioned between $Et_2O$ (30 mL) and $H_2O$ (30 mL). The aqueous phase was extracted with $Et_2O$, then neutralized with 1N NaOH to pH 10. The aqueous phase was re-extracted with $Et_2O$. The combined organics were dried over $MgSO_4$, filtered and concentrated under reduced pressure to provide the desired material.

Step 5: Dimethyl-[2-(4-methyl-2-amino-phenyl)thiazol-4-ylmethyl]amine

Prepared according to compound 5, Step 4 from dimethyl-[2-(4-methyl-2-nitro-phenyl)-thiazol-4-ylmethyl]amine.

Step 6: 1-[2-(4-Dimethylaminomethylthiazol-2-yl)-5-methyl-3-phenyl]-3-(5-methyl-pyrazin-2-yl)-urea Prepared according to Compound 1, Step 5 from compound 7 and dimethyl-[2-(4-methyl-2-amino-phenyl)thiazol-4-ylmethyl]amine. LRMS (apci, positive) m/e 383.0 (M+1).

Therapeutic Methods

Compounds of the present invention can be used to treat conditions involving aberrant cell proliferation. For example, the compounds can be used to potentiate the therapeutic effects of radiation and/or a chemotherapeutic agent used in the treatment of cancers and other cell proliferation indications involving eukaryotic cells, including those in humans and other animals. In general, the present compounds inhibit aberrantly proliferating cells, both cancerous and noncancerous. For example, compounds of the invention can be used to enhance treatment of tumors that are customarily treated with an antimetabolite, e.g., methotrexate or 5-fluorouracil (5-FU).

Use of compounds of the present invention can result in partial or complete regression of aberrantly proliferating cells, i.e., the reduction or elimination of such cells from the cell population. Thus, for example, when the population of aberrantly proliferating cells are tumor cells, compounds of the invention can be used to retard the rate of tumor growth, decrease the number of tumors, and/or induce partial or complete tumor regression.

Compounds of the present invention can be used in vivo or ex vivo when no aberrant cell proliferation has been identified or where no aberrant cell proliferation is ongoing, but when aberrant cell proliferation is suspected or expected. Compounds of the present invention also can be used when aberrant cell proliferation has been previously treated in order to prevent or inhibit recurrence of the same.

One method of the present invention comprises administration of a therapeutically effective amount of a present Chk1 inhibitor compound in combination with a chemotherapeutic agent to an individual in need thereof. Alternatively, a method of the present invention comprises administration of a therapeutically effective amount of at least one of the present Chk1 inhibitors to an individual in need thereof in combination with an antibody, e.g., herceptin, that has activity in inhibiting the proliferation of cancer cells.

Cancers, therefore, are susceptible to enhanced treatment by administration of a present Chk1 inhibitor in combination with a chemotherapeutic agent or an antibody. Cancers treatable by the present invention include carcinomas and sarcomas that are characterized by solid tumors, and cancers of the myeloid or lymphoid systems, including leukemias, lymphomas, and other cancers that typically lack a tumor mass, but are distributed in the vascular or lymphoreticular systems. These cancers include, for example, colorectal cancers, head and neck cancers, pancreatic cancers, breast cancers, gastric cancers, bladder cancers, vulvar cancers, leukemias, lymphomas, melanomas, renal cell carcinomas, ovarian cancers, brain cancers, osteosarcomas, and lung cancers.

Compounds of the present invention, therefore, are useful in cancers mediated by Chk1 activity. More particularly, Chk1 activity is associated with forms of cancer including, but not limited to, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood-cell malignancies, including multiple myeloma, leukemias, including acute lymphocytic leukemia, acute antilymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma), gastrointestinal cancers (including stomach cancer, colon cancer, colorectal cancer, and polyps %: associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, glidmas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

A compound of the present invention also can be used to radiosensitize cells. Diseases treatable with radiation include, but are not limited to neoplastic diseases, benign and malignant tumors, and cancerous cells. Radiation treatment employs electromagnetic radiation such as gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1.0 mm), and microwave radiation (1 mm to 30 cm).

Some cancer treatment protocols currently employ radiosensitizers activated by electromagnetic radiation, e.g., X-rays. Examples of X-ray-activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromideoxycytidine, fluorodeoxyuridine (FUdR), hydroxyurea, cisplatin, and therapeutically effective analogs and derivatives thereof.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to the Chk1 inhibitor, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents or methods that can be used in conjunction with radiosensitizers include, but are not limited to, 5-fluorouracil (5-FU), leucovorin, oxygen, carbogen, red cell transfusions, perfluorocarbons (erg., FLUOSOLW®-DA), 2,3-DPG, BW12C, calcium channel blockers, pentoxifylline, antiangiogenesis compounds; hydralazine, and L-BSO.

Chemotherapeutic agents that can be used in combination with a compound of the present invention to treat a cancer include, but are not limited to, alkylating agents, antimetabolites, hormones and antagonists thereof, radioisotopes, antibodies, as well as natural products, and combinations thereof. For example, an inhibitor compound of the present invention can be administered with antibiotics, such as doxorubicin and other anthracycline analogs, nitrogen-mustards, such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct antineoplastic modalities." Additional chemotherapeutic agents useful in the invention include hormones and antagonists thereof, radioisotopes, antibodies, natural products, and combinations thereof. Examples of chemotherapeutic agents useful in methods employing compounds of the present invention are listed in the following table.

TABLE 1

A) Alkylating agents
    i) Nitrogen mustards
        mechlorethamine
        cyclophosphamide
        ifosfamide
        melphalan
        chloroambucil
    ii) Nitrosoureas
        carmustine (BCNU)
        lomustine (CCNU)
        semustine (methyl-CCNU)
    iii) Ethylenimine/Methyl-melamine
        triethylenemelamine (TEM)
        triethylene thiophosphoramide (thiotepa)
        hexamethylmelamine (HMM, altretamine)
    iv) Alkyl sulfonates
        busulfan
    v) Triazines
        dacarbazine (DTIC)
B) Antimetabolites
    i) Folic Acid analogs
        methotrexate
        trimetrexate
        pemetrexed (multitargeted antifolate)
    ii) Pyrimidine analogs
        5-fluorouracil
        fluorodeoxyuridine
        gemcitabine
        cytosine arabinoside (AraC, cytarabine)
        5-azacytidine
        2,2'-difluorodeoxy-cytidine
    iii) Purine analogs
        6-mercaptopurine
        6-thioguanine
        azathioprine
        2'-deoxycoformycin (pentostatin)
        erythrohydroxynonyl-adenine (EHNA)
        fludarabine phosphate
        2-chlorodeoxyadenosine
        (cladribine, 2-CdA)
C) Type I Topoisomerase inhibitors
    camptothecin
    topotecan
    irinotecan
D) Biological response modifiers
    G-CSF
    GM-CSF
E) Differentiation agents
    retinoic acid derivatives
F) Hormones and antagonists
    i) Adrenocorticosteroids/antagonists
        prednisone and equivalents TABLE 1-continued dexamethasone
        ainoglutethimide
    ii) Progestins
        hydroxyprogesterone caproate
        medroxyprogesterone acetate
        megestrol acetate
    iii) Estrogens
        diethylstilbestrol
        ethynyl estradiol and equivalents
    iv) Antiestrogen
        tamoxifen
    v) Androgens
        testosterone propionate
        fluoxymesterone and equivalents
    vi) Antiandrogens
        flutamide
        gonadotropin-releasing hormone analogs
        leuprolide
    vii) Nonsteroidal antiandrogens
        flutamide
G) Natural products
    i) Antimitotic drugs
    ii) Taxanes
        paclitaxel
        vinca alkaloids
        vinblastine (VLB)
        vincristine
        vinorelbine
        Taxotere (docetaxel)
        estramustine
        estramustine phosphate
    iii) Epipodophylotoxins
        etoposide
        teniposide
    iv) Antibiotics
        actimomycin D
        daunomycin (rubidomycin)
        doxorubicin (adriamycin)
        mitoxantroneidarubicin
        bleomycin
        splicamycin (mithramycin)
        mitomycin C
        dactinomycin
        aphidicolin
    v) Enzymes
        L-asparaginase
        L-arginase
H) Radiosensitizers
    metronidazole
    misonidazole
    desmethylmisonidazole
    pimonidazole
    etanidazole
    nimorazole
    RSU 1069
    EO9
    RB 6145
    SR4233
    nicotinamide
    5-bromodeoxyuridine
    5-iododeoxyuridine
    bromodeoxycytidine
I) Miscellaneous agents
    i) Platinium coordination complexes
        cisplatin
        carboplatin
        oxaliplatin
        anthracenedione
        mitoxantrone
    ii) Substituted urea
        hydroxyurea
    iii) Methylhydrazine derivatives
        N-methylhydrazine (MIH)
        procarbazine
    iv) Adrenocortical suppressant
        mitotane (o,p'-DDD)
        ainoglutethimide TABLE 1-continued J) Cytokines
  interferon (a, β, γ)
  interleukin-2
K) Photosensitizers
  hematoporphyrin derivatives
  Photofrin
  benzoporphyrin derivatives
  Npe6
  tin etioporphyrin (SnET2)
  pheoboride-a
  bacteriochlorophyll-a
  naphthalocyanines
  phthalocyanines
  zinc phthalocyanines
L) Radiation
  X-ray
  ultraviolet light
  gamma radiation
  visible light
  infrared radiation
  microwave radiation Examples of chemotherapeutic agents that are particularly useful in conjunction with radiosensitizers include, for example, camptothecin, carboplatin, cisplatin, daunorubicin, doxorubicin, interferon (alpha, beta, gamma), irinotecan, hydroxyurea, chlorambucil, 5-fluorouracil, methotrexate, 2-chloroadenosine, fludarabine, azacytidine, gemcitabine, pemetrexed, interleukin 2, irinotecan, docetaxel, paclitaxel, topotecan, and therapeutically effective analogs and derivatives of the same.

In accordance with the present invention, compounds of the present invention are useful in combination with gemcitabine, alone or further with paclitaxel. Compounds of the present invention also are useful in combination with pemetrexed, alone or further with cisplatin, carboplatin, or other platins. A present Chk1 inhibitor also can be administered in combination with gemcitabine and pemetrexed.

A present Chk1 inhibitor administered in combination with gemcitabine can be useful in the treatment of, for example, pancreatic carcinoma, leiomyosarcoma of the uterus, bone sarcoma, metastatic nonsmall cell lung cancer, extremity and trunk soft tissue sarcoma, renal cell cancer, adenocarcinoma, and Hodgkin's disease. A present Chk1 inhibitor administered with pemetrexed can be useful in the treatment of mesothelioma.

Compounds of the present invention also can potentiate the efficacy of drugs used in the treatment of inflammatory diseases, conditions, or disorders characterized by aberrant cell proliferation. Examples of inflammatory diseases that can be treated with compounds of the present invention include, but are not limited to, rheumatoid arthritis (RA), psoriasis, vitiligo, Wegener's granulomatosis, systemic-onset juvenile chronic arthritis (JCA), and systemic lupus erythematosus (SLE). Treatment of arthritis, Wegener's granulomatosis, and SLE often involves the use of immunosuppressive therapies, such as ionizing radiation, methotrexate, and cyclophosphamide. Such treatments typically induce, either directly or indirectly, DNA damage. Inhibition of Chk1 activity within the offending immune cells render the cells more sensitive to control by these standard treatments. Psoriasis and vitiligo commonly are treated with ultraviolet radiation (UV) in combination with a psoralen. The compounds of the present invention enhance the killing effect of UV and a psoralen, and increase the therapeutic index of this treatment regimen. In general, compounds of the present invention potentiate control of inflammatory disease cells when used in combination with immunosuppressive drugs.

The compound of the present invention also can be used in methods of treating other noncancerous conditions characterized by aberrantly proliferating cells. Such conditions include, but are not limited to, atherosclerosis, restenosis, vasculitis, nephritis, retinopathy, renal disease, proliferative skin disorders, psoriasis, keloid scarring, actinic keratosis, Stevens-Johnson Syndrome, osteoporosis, hyperproliferative diseases of the eye including epithelial down growth, proliferative vitreoretinbpathy (PVR), diabetic retropathy, Hemangio-proliferative diseases, ichthyosis, and papillomas.

One preferred method of administering a Chk1 inhibitor of the present invention is described in WO 05/027907, the disclosure of which is incorporated by reference. Such methods for inhibiting aberrant cell proliferation involve scheduling administration of a Chk1 activator (e.g., a chemotherapeutic agent) and a Chk1 inhibitor according to the present invention. In this method, at least one Chk1 activator is administered at a dose and for a time sufficient to induce substantial synchronization of cell cycle arrest in proliferating cells. Upon achieving substantial phase synchronization, at least one Chk1 inhibitor is administered to abrogate the cell cycle arrest and induce therapeutic cell death. The method is useful with any Chk1 activator, and finds application in treating or preventing cancerous and noncancerous conditions involving aberrant cell proliferation.

A population of aberrantly proliferating cells can be contacted with one, or more than one, Chk1 inhibitor of the invention. If more than one Chk1 inhibitor is used, the Chk1 inhibitors can be contacted with the cells using the same or different methods (e.g., simultaneously or sequentially, for the same or different durations, or by the same or different modalities) as determined by the skilled artisan, e.g., an attending physician (in the case of human patients) or a laboratory experimentalist (in the case of an in vitro or ex vivo procedure).

A population of aberrantly proliferating cells also can be contacted with one or more Chk1 activator. If more than one Chk1 activator is used, the Chk1 activators can be contacted with the cells using the same or different methods, generally as described in the context of Chk1 inhibitors above.

Compounds of the present invention can be applied to cell populations ex vivo. For example, the present compounds can be used ex vivo to obtain information concerning the optimal schedule and/or dosing for administering a Chk1 inhibitor for a given indication, cell type, patient, and/or other treatment parameter. This information can be used for experimental purposes or in a clinic to determine protocols for in vivo treatment. Other ex vivo uses for compounds of the present invention will be apparent to persons skilled in the art.

As appreciated by persons skilled in the art, additional active or ancillary agents may be used in the methods described herein. As also appreciated by persons skilled in the art, reference herein to treatment extends to prophylaxis, as well as to treatment of established diseases or symptoms.

The amount of a compound of the invention required for use in treatment varies with the nature of the condition being treated, and with the age and the condition of the patient, and is ultimately determined by the attendant physician or veterinarian. In general, however, doses administered for adult human treatment typically are in the range of 0.001 mg/kg to about 100 mg/kg per day. The dose can be administered in a single dose, or as multiple doses administered at appropriate intervals, for example as two, three, four or more subdoses per day. In practice, the physician determines the dosing regimen suitable for an individual patient, and the dosage varies with the age, weight, and response of the particular patient. The above dosages are exemplary of the average case, but individual instances exist wherein higher or lower dosages are merited, and such are within the scope of the present invention.

Contact of the cell population with a present Chk1 inhibitor, at any dose, is for a time sufficient to achieve substantial abrogation of the cell cycle checkpoint. Typically, though not necessarily, such times include up to about 72 h to about 96 h, depending upon various factors. In some embodiments, it is desirable or necessary to administer Chk1 inhibitor over a period of up to about several weeks or more, as determined by the attending physician or technician. Thus, a present Chk1 inhibitor typically can be administered for up to about 1 hour, up to about 2 h, up to about 3 h, up to about 4 h, up to about 6 h, up to about 12 h, up to about 18 h, up to about 24 h, up to about 48 h, or up to about 72 h. Persons skilled in the art appreciate that the ranges of time expressed herein are merely exemplary and that ranges and subranges within and outside those expressed also are within the scope of the invention.

Chk1 inhibitors of the present invention can be administered over a plurality of doses. For example, the Chk1 inhibitor can be given at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

EXAMPLES

Example 1

Determination of $IC_{50}$ Values of the Chk1 Inhibitors

Human Chk1 cDNA was identified and cloned as described previously in WO 99/11795, filed Sep. 4, 1998. A FLAG® tag was inserted in frame with the amino terminus of the full-length Chk1. The 5' primer contains an EcoRI site, a Kozak sequence, and also encodes a FLAG® tag for affinity purification using the M2 Antibody (Sigma, Saint Louis, Ill.). The 3' primer contains a SalI site. The PCR-amplified fragment was cloned into pCI-Neo as an EcoRI-SalI fragment (Invitrogen, Carlsbad, Calif.), then subcloned as an EcoRI-NotI fragment into pFastBacI (Gibco-BRL, Bethesda, Md.). Recombinant baculovirus was prepared as described in the Gibco-BRL Bac-to-Bac manual and used to infect Sf-9 cells grown in CCM3 medium (HyClone Laboratories, Logan, Utah) for expression of FLAG®-tagged Chk1 protein.

FLAG®-tagged Chk1 was purified from frozen pellets of baculovirus-infected SF9 cells. Frozen cell pellets were mixed with an equal volume of 2× lysis buffer containing 100 mM Tris-HCl pH 7.5, 200 mM NaCl, 50 mM B-glycerophosphate, 25 mM NaF, 4 mM $MgCl_2$, 0.5 mM EGTA, 0.2% TWEEN®-20, 2 mM sodium vanadate, 2 mM DTT, and a cocktail of protease inhibitors (Complete mini, Boehringer Mannheim 2000 catalog #1836170). Cells then were dounced 20 times with the loose pestle of a dounce homogenizer and centrifuged at 48,400×g for 1 hour. The M2 affinity was prewashed with 10 column volumes of 50 mM glycine pH 3.5 followed by 20 mM Tris pH 7.5, 150 mM NaCl alternating three times and ending with a Tris NaCl wash. The column then was washed with 25 column volumes of 20 mM Tris pH 7.5, 150 mM NaCl, 0.1% TWEEN®-20, 1 mM EGTA, 1 mM EDTA and 1× complete mini protease tablets. The cleared lysate-then was bound to M2 affinity resin in batch at 4° C. for 4 h. The mixture of resin and lysate then was poured into a column and the flow through collected. The resin was washed with 10 column volumes of 20 mM Tris pH 7.5, 150 mM NaCl, and 3 mM N-octyl glucoside. FLAG®-tagged Chk1 then was eluted from the column with 6 column volumes of cold 20-mM Tris pH 7.5, 150 mM NaCl, 3 mM N-octyl glucoside containing 0.5 mg/mL FLAG® peptide (Sigma, 2000 Catalog #F-3290). Three fractions were collected an analyzed for the presence of FLAG-tagged Chk1.

The assay for Chk1 kinase activity that includes 100 ng purified FLAG®-Chk1 (150 pmol of ATP/min), 20 μm Cdc25C peptide (H-leu-tyr-arg-ser-pro-ser-met-pro-glu-asn-leu-asn-arg-arg-arg-arg-OH) (SEQ ID NO: 1), 4 μm ATP, 2 μCi [$^{32}$P]γ-ATP, 20 mM Hepes pH 7.2, 5 mM $MgCl_2$, 0.1% NP40, and 1 mM DTT. Reactions were initiated by the addition of ATP-containing reaction mix and carried out at room temperature for 10 min. Reactions were stopped by the addition of phosphoric acid (150 mM final concentration) and transferred to phosphocellulose discs. The phosphocellulose discs were washed five times with 150 mM phosphoric acid and air-dried. Scintillation fluid was added and discs were counted in a Wallac scintillation counter. The assay was incubated in the presence of a broad range of concentrations of Chk1 inhibitor-compound and an $IC_{50}$ value for the compound was calculated. As indicated above, all compounds of the invention subjected to the assay exhibited $IC_{50}$ values in the assay of less than about 500 nM.

Example 2

Selectivity

Chk1 inhibitors of the present invention were tested for selectivity, with Chk1 as the comparison enzyme and the following protein kinases as comparator enzymes: Cdc2, Chk2, CTAK, EphA1, EphA2, Erk1, FGFR1, FGFR4, IR, JNK1, c-Kit, p38alpha, p38beta, p38delta, Ros, Rse, Rsk2, TrkA, TrkB, protein kinase A, protein kinase C, pp60v-src, protein kinase B/Akt-1, p38MapK, p70S-6K, calcium calmodulin-dependent kinase II, and ab1 tyrosine kinase.

The $IC_{50}$ value of a compound versus Chk1 was measured as described above. The $IC_{50}$ value of the compound against comparator enzymes was measured using the SelectSmart™ (MDS Pharma Servies, Bothell, Wash., USA) proprietary technology platform with either a modified ELISA procedure or fluorescence polarization. All inhibitors tested showed at least a 20-fold selectivity for Chk1 over the tested comparator enzymes.

Alternatively, assays for determining $IC_{50}$ for each of these kinases have been previously described in the literature, including U.S. Patent Publication No. 2002/016521 and WO 95/19988, both of which are incorporated by reference here.

Example 3

Chk1 Inhibitors of the Invention Inhibit Chk1 Function in Cells

To establish that the Chk1 inhibitors of the invention inhibit Chk1 function in cells, inhibitors can be tested in molecular cell-based assays. Because mammalian Chk1 has been shown to phosphorylate Cdc25C in vitro, suggesting that it negatively regulates cyclin B/cdc2 in response to DNA damage, the ability of the Chk1 inhibitors to enhance the activity of CyclinB/cdc2 can be analyzed. The experiment can be designed as follows: HeLa cells are irradiated with 800 rads and incubated for 7 h at 37° C. Because these cells are functionally p53 negative, they arrest exclusively in G2. Then, nocodazole is added to a concentration of 0.5 μg/mL and the cells are incubated for 15 h at 37° C. The addition of nocodazole is designed to trap any cells that progress through the G2 arrest into M. Finally, a Chk1 inhibitor is added for 8 h, the cells harvested, lysed and immunoprecipitated equal amounts of protein with an antibody to Cyclin B1 (New England Biolabs) as suggested by the manufacturer. Immunoprecipitates then are analyzed for Cyclin B-associated cdc2 kinase activity by assaying histone H1 kinase activity (Yu et al., *J Biol. Chem.*, Dec. 11, 1998; 273(50):33455-64).

In addition, the ability of the subject Chk1 inhibitors to abrogate the ionizing radiation-induced G2 DNA damage checkpoint can be established using mitotic index assay experiments. HeLa cells (approximately $1\times10^6$) are treated as described above. Cells are harvested by centrifugation, washed once with PBS, then resuspended in 2.5 mL of 75 mM KCl and centrifuged again. The cells then are fixed in 3 mL of freshly prepared cold HOAc:MeOH (1:3) and incubated on ice for 20 min. Cells are pelleted, fix solution aspirated and resuspended in 0.5 mL of PBS. Mitotic spreads are prepared by pipetting 100 µL of the fixed cells onto a glass microscope slide and flooding the sample with 1 mL of fix solution. Slides then are air dried, stained with wright's stain (Sigma) for 1 min, followed by one wash with $H_2O$ and one wash with 50% MeOH. The presence of condensed chromosomes and lack of nuclear envelope identifies mitotic cells.

Example 4

Chk1 Inhibitors of the Present Invention Enhance Killing of Cells by Cancer Treatments To demonstrate that the inhibition of Chk1 by a compound of the present invention sensitizes targeted cells to the killing effect of DNA-damaging agents, cells can be incubated in the presence of a present Chk1 inhibitor and exposed to either irradiation or a chemical DNA-damaging agent. Cells plated at a density of 1000-2000 per well in 96-well microtitre plates are grown in RMPI 1640 containing 10% FBS, 100 U/mL penicillin and 100 µg/mL streptomycin for 18 h at 37° C. in a humidified incubator with 5% $CO_2$. Cells tested can include any cells or cell lines of interest, such as HeLa, ACHN, 786-0, HCT116, SW620, HT29, Colo205, SK-MEL-5, SK-MEL-28, A549, H322, OVCAR-3, SK-OV-3, MDA-MB-231, MCF-7, PC-3, HL-60, K562, and MOLT4. All cell line designations refer to the following human cell lines:

| | |
|---|---|
| HeLa | cervical adenocarcinoma |
| ACHN | renal adenocarcinoma |
| 786-0 | renal adenocarcinoma |
| HCT116 | colon carcinoma |
| SW620 | colon carcinoma, lymph node metastasis |
| HT-29 | colonrectal adenocarcinoma |
| Colo205 | colon adenocarcinoma |
| SK-MEL-5 | melanoma |
| SK-MEL-28 | malignant melanoma |
| A549 | lung carcinoma |
| H322 | broncholoalveolar carcinoma |
| OVCAR-3 | ovarian adenocarcinoma |
| SK-OV-3 | ovarian adenocarcinoma |
| MDA-MB-231 | breast adenocarcinoma |
| MCF-7 | breast adenocarcinoma |
| PC-3 | prostate adenocarcinoma, from metastasis to bone |
| HL-60 | acute promyelocytic leukemia |
| K562 | chronic myelogenous leukemia |
| MOLT4 | acute lymphoblastic leukemia; T lymphoblast |

Cells are treated with media containing chemotherapeutic drugs-alone or chemotherapeutic drugs and a Chk1 inhibitor. Cells are incubated for approximately 5 days before growth is measured by determination of levels of $^3$H-thymidine uptake. Chemotherapeutic drugs include etoposide, doxorubicin, cisplatin, chlorambucil, 5-fluorouracil. The drug concentration necessary to inhibit cell growth to 90% of untreated control cells is defined as the $GI_{90}$.

Compounds of the present invention can be tested with additional antimetabolites, including methotrexate, hydroxyurea, 2-chloroadenosine, fludarabine, azacytidine, and gemcitibine to assess therein ability to enhance killing of the agents. Compounds of the present invention can be compared to one another by assessing enhanced killing of HT29 colorectal carcinoma in combination with gemcitibine.

In addition, the ability of the Chk1 inhibitors of the invention to enhance killing by radiation can be tested.

Example 5

Sensitive Assay to Measure Chk1 Inhibitor Activity in Animal Models

The following sensitive assay was developed to measure Chk1 inhibitor activity in rodent tumor models. In particular, the assay can be used, inter alias to measure the ability of a Chk1 inhibitor to block Chk1 function in the tumor model, and to allow for assessment of conditions that facilitate access of the Chk1 inhibitor to the molecular target.

The ability of selective Chk1 inhibitors to abrogate a chemotherapy-induced checkpoint is measured using a quantitative immunofluorescent assay that measures mitotic index by monitoring histone H3 phosphorylation on serine 10 (H3-P), a mitosis-specific event (Ajiro et al., *J Biol. Chem.*, 271: 13197-201, 1996; Goto et al., *J Biol. Chem.*, 274:25543-9, 1999). The assay protocol is as follows. Tumors from rodents treated or untreated with Chk1 activator (in the present study, chemotherapy agent) and/or Chk1 inhibitor, are excised and paraffin embedded. The tumors are cut into 6 micron thick slices and mounted on glass slides. The paraffin is removed from the slides by 3 min successive treatments with xylene, 100% ethanol, 95% EtOH, 70% EtOH, and DI $H_2O$. The slides then are heated to 95° C. in 10 mM sodium citrate for 10 min followed by a 20 min cooling step. The slides are blocked for 30 min with Block buffer (20% normal human serum and 2% bovine serum albumin in phosphate buffered, saline containing 0.05% Triton X-100 (PBST)). The antiphospho histone H3 antibody (Upstate Biotech, Cat. #06-570) is diluted 1:200 in the Block buffer and incubated with the slides for 1 h. The slides are washed 3 times 5 min in PBST. The secondary antibody, donkey antirabbit rhodamine (Jackson, cat #711-295-152) is added for 30 min. The slides then are washed twice in PBST and 75 µM of 0.1 µM/ml DAPI (Sigma) in PBS is added and allowed to stain for 30 min. The slides then are washed two more times in PBST and mounted with Vectashield (Vector, cat #H-1400). Slides are viewed using fluorescence microscopy. The percentage of cells stained with H3-P antibody relative to total (DAPI stained) cells are quantified using Metamorph software (Universal Imaging Corporation, Version 4.6).

Example 6

Selective Chk1 Inhibitors Abrogate DNA Damage-Induced G2 and S Phase Checkpoints Previous studies demonstrated that selective Chk1 inhibitors substantially abrogate the DNA damage-induced G2/M and S phase checkpoints. In the former, DNA damage is induced by ionizing radiation (IR), whose target phase is the G2 phase. In the latter, DNA damage is induced by chemotherapeutic agents whose target phase is the S phase. See published U.S. Patent Application Publication 2003/0069284 and references cited therein.

Briefly, Chk1 inhibitor abrogation of IR-induced G2 DNA damage checkpoint is assayed by mitotic index experiments. Approximately $1 \times 10^6$ HeLa cells are irradiated with 800 rads and incubated for 7 h at 37° C. Because these cells are functionally p53 negative, they arrest exclusively in G2. Nocodazole then is added to a concentration of 0.5 µg/mL and incubated for 15 h at 37° C. (The addition of nocodazole is designed to trap cells that progressed through the G2 arrest in mitosis thus preventing them from further progressing into G1 and allowing for quantification of M phase cells.) A selective Chk1 inhibitor is added for 8 h, and the cells are harvested by centrifugation, washed once with PBS, then resuspended in 2.5 mL 75 mM KCl and centrifuged again. The cells then are fixed in 3 mL of freshly prepared cold HOAc:MeOH (1:3) and incubated on ice for 20 min. Cells are pelleted, the fix solution is aspirated and the cells are resuspended in 0.5 mL of PBS. Mitotic spreads are prepared by pipetting 100 µL of the fixed cells onto a a is glass microscope slide and flooding the sample with 1 ml of fix solution. Slides then are air dried, stained with Wrights stain (Sigma, St. Louis, Mo.) for 1 min, followed by one wash in water and one wash in 50% MeOH. The presence of condensed chromosomes and lack of nuclear envelope identified mitotic cells. Chk1 inhibitors result in an increase in the number of mitotic cells in the presence of irradiation, thereby demonstrating abrogation of the IR-induced G2 arrest. This checkpoint abrogation results in an enhancement in the activity of CyclinB/cdc2, which is required for progression of cells into mitosis. Cells treated with IR followed by Chk1 inhibitor thus progress into mitosis with damaged DNA. These experiments confirm the hypothesis that Chk1 is involved in the IR-induced G2.

Example 7

Chk1 Inhibitor is Taken Up by Tumor Cells in the Presence of Chk1 Activator in a Xenograft Tumor Model In a xenograft tumor model, nude mice are engrafted with HT29 colon carcinoma tumors on the flank and allowed to grow to 200 mm$^3$. Mice then are treated with either vehicle, 300 mg/kg Chk1 inhibitor, 20 mg/kg gemcitabine or coadministered with 300 mg/kg Chk1 inhibitor and 20 mg/kg gemcitabine two times, three days apart on Days 1 and 4. Treatment of tumor-bearing mice by co-administration of Chk1 inhibitor and gemcitabine results in a four-day growth delay in tumors compared to gemcitabine alone.

To assess the diffusion of Chk1 inhibitors into tumor tissue, plasma and tissue levels of Chk1 inhibitor are measured. Using an Alzet pump, 500 mg/kg Chk1 inhibitor is administered to HT29 tumor-bearing mice in a continuous delivery system over a 24 h period. Plasma samples are taken, then tumors, kidney, liver, spleen, and lung are harvested. Time points are collected at 1, 2, 4, 8, and 24 h. Tissues are extracted and levels of Chk1 inhibitor are quantified. This experiment demonstrates that a Chk1 inhibitor penetrated into normal and tumor tissue, reaches a level of about 15 µM in tumor tissue, and peaks in spleen tissue at 8 h at about 20 µM. Thus, Chk1 inhibitors were readily taken up by the proliferating cells and are useful, in conjunction with Chk1 activating chemotherapeutic agents, as therapies for the treatment of proliferative diseases.

Example 8

Dose Response of Tumors Treated with Chk1 Inhibitors and Gemcitabine

To determine an efficacious dose of Chk1 inhibitor following gemcitabine treatment and whether the dose-dependent checkpoint abrogation correlated with antitumor activity, a dose response experiment is performed.

Nude mice are engrafted with HT29 tumor cells and tumors allowed to develop for 10 days. The tumors at the start were approximately 100 mm$^3$. Animals were treated with gemcitabine at the MTD (160 mg/kg) followed by Chk1 inhibitor at 50 mg/kg, 200 mg/kg, or 400 mg/kg. Gemcitabine pretreatment time is 32 h in this experiment as determined by a cell-based assay that indicated this timepoint as optimal for this type of tumor. Analysis of tumor volume in each treatment regimen indicated that treatment of HT29 tumor bearing mice with the described therapy slows tumor growth-greater than gemcitabine alone, with either 200 mg/kg or 400 mg/kg Chk1 inhibitor plus gemcitabine again showing dose-dependent effects of the Chk1 inhibitor.

Example 9

Assay to Determine Whether an Agent is a Chk1 Activator

To determine whether an agent is a Chk1 activator, the phosphorylation state of Chk1 can be measured using phospho-specific antibodies to specific phosphorylation sites on Chk1. Serines 317 and 345 have been shown to be phosphorylated after treatment of cells with ionizing radiation, ultraviolet radiation, hydroxyurea, N-methyl-N'-nitro-N-nitrosoguanidine (MNNG), temozolamide and gemcitabine. Liu et al., *Genes Dev.* 14:1448-59, 2000; Zhao et al., *Mol. Cell. Biol.* 21:4129-39, 2001; Lopez-Girona et al., *Proc. Natl. Acad. Sci. U.S.A.* 98:11289-94, 2001; Guo et al., *Genes Dev.* 14:2745-56, 2000; Gatei et al., *J. Biol. Chem.* 278:14806-11, 2003; Ng et al., *J Biol. Chem.* 279(10):8808-19, 2004; Wang et al., *Natl Acad Sci USA.* 100(26):15387-92, 2003; Stojic et al., *Genes Dev.* 18(11):1331-44, 2004. These serine sites are phosphorylated by upstream checkpoint kinases, Atm and Atr. Liu et al., *Genes Dev.* 14:1448-59, 2000; Zhao et al. *Mol. Cell. Biol.,* 21:4129-39, 2001).

The phosphorylation of these sites in response to a candidate Chk1 activator can be monitored by Western blot or immunohistochemistry of tumor cells. For example, the following procedure can be used to demonstrate that gemcitabine results in Chk1 activation at serine 345 and 317. HT29 cells are treated with 20 µM gemcitabine for two h. The gemcitabine is washed out of the cell growth media and cells are incubated for 22 additional h. Protein lysates are prepared and separated by an SDS-polyacrylamide gel electrophoresis. Proteins are transferred to PVDF membranes and probed with antisera (Cell Signalling) specific for either phosphorylated serine 317 or 345 (Cell Signalling). Western blots show that gemcitabine treatment of HT29 colon carcinoma cells results in the phosphorylation of both serines 317 and 345.

Example 10

Assay to Monitor Chk1 Activity in Response to a Chk1 Inhibitor

It has been found that phosphorylation of Chk1 at serine 296 is stimulated by treatment of tumor cells with gemcitabine, and that phosphorylation at this site is inhibited by Chk1 inhibitors. Phosphorylation at this site is not inhibited by wortmannin, which inhibits Atm and Atr. Therefore, the phosphorylation of serine 296 is distinct from phosphorylation at serines 317 and 345. In addition, it has been found that this site is phosphorylated in purified Chk1 preparations, suggesting that the purified enzyme is able to phosphorylate itself or other Chk1 molecules at serine 296. Taken together, these data suggest that phosphorylation at serine 296 is performed by Chk1 itself. Therefore, this approach can be used to monitor Chk1 activity in tumors in response to Chk1 activators. Further, this approach can be used to measure inhibition of Chk1 activation by Chk1 inhibitors.

Thus, HT 29 cells are treated with 20 μM gemcitabine for two h. The gemcitabine is washed out of the cell growth media and cells are incubated for 22 additional h. Protein lysates are prepared and separated by an SDS-polyacrylamide gel electrophoresis. Proteins are transferred to polyvinylidene fluoride (PVDF) membranes and probed with antisera (Cell Signalling) specific for phosphorylated serine 296 (Cell Signalling). Western blot shows that gemcitabine treatment of HT29 colon carcinoma cells results in the phosphorylation of serine 296. Further, HT29 cells treated with selective Chk1 inhibitors for 15 min show no serine 296 phosphorylation. These data suggest that serine 296 phosphorylation is performed by the Chk1 kinase.

Example 11

Animal Tumor Models

To test the ability of the Chk1 inhibitors of the invention to enhance the killing of tumors by DNA damaging agents in mice, xenograft tumor models using colon tumor cell lines are established. 5-fluorouracil (5-FU) or gemcitabine can be used as DNA damaging agents; HT29 and Colo205 (human colon carcinoma) and H460 and Calu-6 (nonsmall cell carcinoma) cells can be used to propagate xenograft tumors in 6-8 week old female thymic Balb/c (nu/nu) mice. Mice are maintained in a laminar airflow cabinet under pathogen-free conditions and fed sterile food and water ad libitum. Cell lines are grown to subconfluence in RPMI 1640 media supplemented with 10% FBS, 100 U/mL penicillin, 100 μg/mL streptomycin, and 1.5 mM L-glutamine in a 5% $CO_2$ humidified environment. Single cell suspensions are prepared in CMF-PBS, and cell concentration adjusted to $1\times10^8$ cells/mL. Mice are inoculated subcutaneously (s.c.) on the right flank or right leg with a total of $1\times10^7$ cells (100 μL).

Mice are randomized (5-15 mice/group) into four treatment groups and used when tumors reach a volume of 75-100 $cm^3$ (usually 7-11 days post-inoculation). Tumors are measured with vernier calipers and tumor volumes are estimated using the empirically derived formula: tumor volume ($cm^3$) =tumor length (cm)×tumor width (cm)×tumor depth (cm)/3.3. Treatment consists of i) 100 μL intraperitoneal (i.p) injection of gemcitabine at 160 mg/kg. A delay in tumor growth is observed in the mice treated with gemcitabine. Treatment of mice with both 160 mg/kg gemcitabine in combination with oral administration of Chk1 inhibitors is expected to reduce tumor volumes and prolong life. Tumor size is monitored every other day for the duration of the experiment.

Obviously, many modifications and variations of the invention as hereinbefore set forth can be made without departing from the spirit and scope thereof, and, therefore, only such limitations should be imposed as are indicated by the appended claims.

---

---

What is claimed is:
1. A compound having a formula

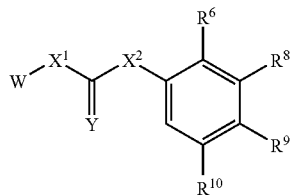

wherein $X^1$ and $X^2$ are —N(H)—;
Y is O;
W is pyrazinyl substituted with $CH_3$;
$R^6$ is selected from the group consisting of

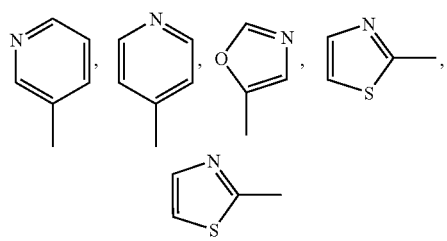

substituted with $C_{1-3}$alkyleneNH($CH_3$)$_2$, and —C≡C—$R^7$;
$R^7$ is pyridinyl;

R⁸, R⁹, and R¹⁰ are hydro, alternatively, R⁸ and R⁹ are hydro when R¹⁰ is CH$_3$;

or a pharmaceutically acceptable salt thereof.

2. A pharmaceutical composition comprising a compound of claim 1, or a pharmaceutically acceptable salt thereof, together with a pharmaceutically acceptable diluent or carrier.

3. A compound selected from the group consisting of:
1-(5-methyl-pyrazin-2-yl)-3-(5-methyl-2-pyridin-3-yl-ethynyl-phenyl)-urea;
1-(5-methyl-pyrazin-2-yl)-3-(5-methyl-2-pyridin-3-yl-phenyl)-urea;
1-(5-methylpyrazin-2-yl)-3-(5-methyl-2-pyridin-4-yl-phenyl)-urea;
1-(5-methyl-pyrazine-2-yl)-3-(2-oxazol-5-yl-phenyl)-urea;
1-(5-methyl-pyrazin-2-yl)-3-(5-methyl-2-thiazol-2-ylphenyl)-urea; and
1-[2-(4-dimethylaminomethyl-thiazol-2-yl)-5-methyl-phenyl]-3-(5-methyl-pyrazin-2-yl)-urea.

* * * * *

SEQUENCE LISTING

<160> NUMBER OF SEQ ID NOS: 1

<210> SEQ ID NO 1
<211> LENGTH: 16
<212> TYPE: PRT
<213> ORGANISM: artificial
<220> FEATURE:
<223> OTHER INFORMATION: synthetic peptide

<400> SEQUENCE: 1

Leu Tyr Arg Ser Pro Ser Met Pro Glu Asn Leu Asn Arg Arg Arg Arg
1               5                   10                  15